(12) United States Patent
Chen et al.

(10) Patent No.: US 9,901,615 B2
(45) Date of Patent: Feb. 27, 2018

(54) METHOD FOR TREATMENT OF GASTRIC ULCERS

(71) Applicants: Academia Sinica, Taipei (TW); National Taiwan Ocean University, Keelung (TW)

(72) Inventors: Jyh-Yih Chen, Ilan (TW); Chang-Jer Wu, Ilan (TW)

(73) Assignees: ACADEMIA SINICA, Taipei (TW); NATIONAL TAIWAN OCEAN UNIVERSITY, Keelung (TW)

( * ) Notice: Subject to any disclaimer, the term of this patent is extended or adjusted under 35 U.S.C. 154(b) by 0 days.

(21) Appl. No.: 15/098,486

(22) Filed: Apr. 14, 2016

(65) Prior Publication Data

US 2016/0303190 A1     Oct. 20, 2016

Related U.S. Application Data

(60) Provisional application No. 62/147,308, filed on Apr. 14, 2015.

(51) Int. Cl.
*A61K 38/17* (2006.01)
*C07K 14/435* (2006.01)
*A61P 31/04* (2006.01)

(52) U.S. Cl.
CPC ................................. *A61K 38/1706* (2013.01)

(58) Field of Classification Search
CPC .................................................. A61K 38/1706
See application file for complete search history.

(56) References Cited

PUBLICATIONS

DiMarino, *Helicobacter pylori* Infection, from Merck Manual, May 2014, pp. 1-4.*
Ayala et al, Exploring Alternative Treatments for *Helicobacter pylori* Infection, World J Gastroenterol, 2014, 20, pp. 1450-1469.*
Zhang et al, The Synthetic Antimicrobial Peptide Pexiganan and Its Nanoparticles (PNPs) Exhibit the Anti-Helicobacter pylori Activity in Vitro and in Vivo, Molecules, 2015, 20, pp. 3972-3985.*
Makobongo et al, The Oligo-Acyl Lysyl Antimicrobial Peptide C12K-2beta12 Exhibits a Dual Mechanism of Action and Demonstrates Strong In Vivo Efficacy against Helicobacter pylori, Antimicrobial Agents and Chemotherapy, 2012, 56, pp. 378-390.*
Giuliani et al, Antimicrobial peptides: an overview of a promising class of therapeutics, CEJB, 2007, 2, pp. 1-33.*
Jones et al, Who's Winning the War? Molecular Mechanisms of Antibiotic Resistance in Helicobacter pylori, Curr Drug Ther., 2008, 3, pp. 190-203.*
Peng et al, Five Different Piscidins from Nile Tilapia, Oreochromis niloticus: Analysis of Their Expressions and Biological Functions, PLoS One, 2012, 7, pp. 1-12.*

* cited by examiner

*Primary Examiner* — Julie Ha
*Assistant Examiner* — Li Ni Komatsu
(74) *Attorney, Agent, or Firm* — Juan Carlos A. Marquez; Marquez IP Law Office, PLLC

(57) ABSTRACT

The preset invention relates to a new method or composition for treating a gastric ulcer, preventing or treating an infection of *H. pylori*, particularly multidrug resistant *H. pylori*, using an antimicrobial peptide, a functional derivate, fragment or variant thereof, wherein the antimicrobial peptide is selected from the group consisting of Epi-1, TPs and combination thereof.

4 Claims, 20 Drawing Sheets ent application claims priority under 35 U.S.C.
METHOD FOR TREATMENT OF GASTRIC ULCERS

RELATED APPLICATION

The present application claims priority under 35 U.S.C. § 119(e) to U.S. Provisional Patent Application No. 62/147,308, filed Apr. 14, 2016, the content of which is herein incorporated by reference in its entirety.

SEQUENCE LISTING

The present application contains a Sequence Listing which is being submitted electronically in ASCII format concurrently herewith, and is hereby incorporated by reference in its entirety. Said ASCII copy is named "LEXC-3_Amended_Sequence_Listing_06232016.txt" and is 4 kilobytes in size.

FIELD OF THE INVENTION

The present invention relates to a new method or composition for treating gastric ulcers.

BACKGROUND OF THE INVENTION

The discovery of *Helicobacter pylori* (*H. pylori*) and its role in gastric ulcers triggered a revolution in gastroenterology research (Megraud et al., Helicobacter pylori resistance to antibiotics in Europe and its relationship to antibiotic consumption. Gut. 2013; 62:34-42; Arias & Murray, Antibiotic-resistant bugs in the 21st century—a clinical super-challenge. The New England journal of medicine. 2009; 360:439-43). *H. pylori* is one of the most ubiquitous bacterial pathogens in humans, and it has colonized the stomachs of as many as half of the global human population. This pathogen may cause a variety of gastroduodenal diseases, including gastritis, peptic ulcer, MALT lymphoma, and gastric cancer (Fock et al., Helicobacter pylori research: historical insights and future directions. Nature reviews Gastroenterology & hepatology. 2013; 10:495-500). However, various attempts to develop preventive vaccines against *H. pylori* have failed. In the event that infection is diagnosed, *H. pylori* is treated with conventional antibiotic regimens. However, the success rate of these treatments is compromised by the drastic increase of antimicrobial resistant strains of *H. pylori* (Rimbara E, Fischbach L A, Graham D Y. Optimal therapy for Helicobacter pylori infections. Nature reviews Gastroenterology & hepatology. 2011; 8:79-88; Marshall B J, Warren J R. Unidentified curved bacilli in the stomach of patients with gastritis and peptic ulceration. Lancet. 1984; 1:1311-5). Many classical antibiotics are ineffective at eradicating *H. pylori*. The early 1990's saw the beginning of triple therapy regimens against such infection. Recently, however, emerging resistance against the most clinically-important antibiotics, metronidazole and clarithromycin, has had a major detrimental effect on the efficiency of triple therapy; furthermore, an increase in the frequency of resistant strains would limit the use of these antibiotics in future regimens, because resistance cannot be overcome by increasing the dose or duration of treatment (Fischbach L, Evans E L. Meta-analysis: the effect of antibiotic resistance status on the efficacy of triple and quadruple first-line therapies for Helicobacter pylori. Alimentary pharmacology & therapeutics. 2007; 26:343-57; Megraud F. H. pylori antibiotic resistance: prevalence, importance, and advances in testing. Gut. 2004; 53:1374-84).

It is still desirable to develop a new drug or an alternative drug regimen for treating gastric ulcers or *H. pylori* infections.

SUMMARY OF THE INVENTION

It is unexpectedly found that two antimicrobial peptides, Epinecidin-1 (Epi-1) and tilapia piscidins, particularly tilapia piscidin 4 (TP4), are effective against different *H. pylori* strains, including multi-drug resistant *H. pylori*.

Accordingly, in one aspect, the present invention provides a method for treating a gastric ulcer comprising administering a subject in need thereof with a therapeutically effective amount of an antimicrobial peptide, a functional derivate, fragment or variant thereof.

In another aspect, the present invention provides a method for preventing or treating an infection of *H. pylori*, comprising administering a subject in need thereof with a therapeutically effective amount of an antimicrobial peptide, a functional derivate, fragment or variant thereof.

In one further aspect, the present invention provides a method for preventing or treating an infection of multidrug resistant *H. pylori*, comprising administering a subject in need thereof with a therapeutically effective amount of an antimicrobial peptide, a functional derivate, fragment or variant thereof.

In one embodiment of the invention, the antimicrobial peptide is selected from the group consisting of Epi-1, TPs and combination thereof. Particularly, TP is TP4.

In one yet aspect, the present invention provides a composition or a pharmaceutical composition for preventing or treating an infection of *H. pylori* comprising a therapeutically effective amount of an antimicrobial peptide, a functional derivate, fragment or variant thereof, in which the antimicrobial peptide is selected from the group consisting of Epi-1, TPs and combination thereof.

In one more aspect, the present invention provides a composition or a pharmaceutical composition for preventing or treating an infection of multidrug resistant *H. pylori* comprising a therapeutically effective amount of an antimicrobial peptide, a functional derivate, fragment or variant thereof, in which the antimicrobial peptide is selected from the group consisting of Epi-1, TPs and combination thereof.

In one further yet aspect, the present invention provides a use of an antimicrobial peptide, a functional derivate, fragment or variant thereof, for manufacturing a medicament for treating a gastric ulcer.

In one more further aspect, the present invention provides a use of an antimicrobial peptide, a functional derivate, fragment or variant thereof, for manufacturing a medicament for preventing or treating an infection of *H. pylori*.

In one more further yet aspect, the present invention provides a use of an antimicrobial peptide, a functional derivate, fragment or variant thereof, for manufacturing a medicament for preventing or treating an infection of multidrug resistant *H. pylori*.

In one embodiment of the invention, the antimicrobial peptide is selected from the group consisting of Epi-1, TPs and combination thereof.

In one particular example of the invention, TP is TP4.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

In FIG. 3, the image (a) shows the group of the untreated *H. pylori*; the image (b) shows the cells treated with amoxicillin, in which increased cell death and decreased cells in the coccoid form were found; the image (c) shows the group of the Epi-1 exposure causing complete membrane lysis, resulting in leakage of cellular contents and subsequent cell death; the image (d) shows the high magnification images revealing blebs on the membrane (large arrow), indicative of saddle-splay membrane curvature generation; and the image (e) shows the Epi-1 inducing distortion of *H. pylori* by membrane blebbing, lysis of the membrane, and loosening of the outer membrane after lysis, which induced excess periplasmic space and subsequent osmotic imbalance in this region; wherein magnification in electron micrographs: (a)-(c) ×2,550, (d) ×15,000, (e) ×7,000. Scale Bar=0.2 μm.

FIG. 10A shows dermal toxicity: Epi-1 (2.5 mg/animal every day for 7 days; n=12 per group) was applied to the indicated area (dotted oval) of Balb/c mice; and FIG. 10B shows Eye irritation test: rabbit eyes were exposed to Epi-1 (1 mg/rabbit) every day for 7 days. SDS was used as positive control to evaluate the abnormality scores; PBS was used as a negative control (n=2).

FIG. 11A shows the dose- and time-dependent killing kinetics, wherein approximately, $2 \times 10^5$ cells were incubated for 1 h, and then incubated with the indicated concentrations (¼, ½, 1, 2, and 4 fold of MIC) of TP4, and control peptide and *H. pylori* alone were used as controls; in which the cultures were monitored for 24 h, and aliquots were taken at 1, 3, 6, 12, and 24 h to determine surviving CFU. FIG. 11B shows the results of the *H. pylori* cells incubated for 1 h, and then incubated with the MIC of TP4, AMOX, METZ, and CLRN; wherein the cultures were monitored for 24 h, and aliquots taken at 1, 3, 6, 12, and 24 h to determine surviving CFU. FIG. 11C shows the effect of TP4 on in vitro and in vivo passage induced resistance of *H. pylori*. FIG. 11D shows the synergistic effect of TP4 in combination with AMOX, METZ, and CLRN. MICs: standard MIC value; MICp: passage induced MIC (all data representative are means±SEM).

FIG. 12A shows that TP4 rapidly permeabilizes the *H. pylori* outer membrane in a dosed dependent manner; the correlation of membrane disruption was examined by uptake of 1-N-phenylnaphthylamine fluorescence intensity. *H. pylori* alone, or with NPN/control peptide were used as controls. FIG. 12B shows Zeta-potential of *H. pylori* in the presence/absence of TP4 (Striped bars: *H. pylori* grown in blood agar plates; white bar: liquid culture; the data shown are means±SEM). FIG. 12C shows the electron micrographs revealing that TP4 causes membrane disruption in *H. pylori* via micellization; wherein Column (a) shows *H. pylori* cells in PBS; normal spiral and comma shaped morphology; Column (b) shows 1×MIC amoxicillin; few ghost cells/dead cells and induced coccoid forms of *H. pylori*; Column (c) TP4 exposed cells appearance of abundant 'ghost/dead' cells due to membrane lysis; the upper panels at low (1,100×) or lower panels with high magnification. (5,500×). FIG. 12D shows the TP4 induced micellization of the *H. pylori* membrane: The image (a) at 7,000× magnification reveals characteristic *H. pylori* membrane disruption; the image (b) and (c) at 15,000× magnification show short round arrowheads: micelles formation sites, arrow heads: nick regions where micellization initiates, short arrows: missing membrane sections, and long arrows: electron dense aggregates inside cells probably nucleic acids (Scale bars: FIG. 12D: (a) 200 nm; (b) and (c) 100 nm).

FIG. 13A shows the experimental plan, wherein mice were orally infected with approximately $1 \times 10^9$ CFU of *H. pylori* on days 1 and 3. On day 9, mice were euthanized and confirmed infection rate; animals were divided into three groups: (i) *H. pylori* infection alone; (ii) infection and treatment with TP4 treatment; and (iii) infection and treatment with triple therapy antibiotics. The groups were given orogastric doses of (ii) TP4 (200 µg/animal) and (iii) 10×MIC of PPI-Triple therapy complex for two weeks; later, mice were euthanized, and stomach, spleen, and blood were harvested for use in various cytological and biochemical assays. FIG. 13B shows the results of the rapid urease test for *H. pylori* identification in gastric tissue lysate, including the group of untreated (top panel), the group of TP4 treated (middle panel), and the group of PPI-triple therapy treated (bottom panel); in which pink spots indicate *H. pylori* infection: Right: cultured selective media plates. FIG. 13C shows the enumeration of bacterial burden in the stomachs of *H. pylori*-infected, treated with TP4 or triple therapy (n=6). FIG. 13D shows the effects of TP4 on *H. pylori* virulence factors, wherein (a) gene and protein expression of Type IV secretory CagA and Urease B were examined; untreated (left column), or TP4 treated (middle column) or PPI-triple therapy (right column); (b) Western blot analysis of urease protein in gastric tissue lysates (bars represent median values. $p<0.05$, * $p<0.001$. (n=6)).

FIG. 15B showing the gene expression analysis by real-time PCR for gastric tissues (data are representative means±SEM).

FIG. 17A provides the results of the eye irritation, including the ocular appearances of controls, and rabbits treated with 50 mg/kg TP4 or SDS for 7 days; wherein the animals were observed daily, and no ocular lesions were detected in the control or TP4-treated rabbits; the positive control SDS caused severe lacrimation, swelling of the eyelids, and elevated blood vessels in conjunctivae (arrow). In FIG. 17A, the lower panel shows fluorescein stain images. FIG. 17B shows the dermal toxicity, including the appearances of the skin of mice treated with TP4 at 48 h post-exposure; in which no obvious lesions were observed in mice treated with 125 mg/kg TP4 or 20% SDS after residue removal; TP4 exposure was extended for 7 days, and animals were observed daily until day 14; no clumps or lesions were observed in TP4-treated mice at the end of the study (n=12 per group).

DETAILED DESCRIPTION OF THE INVENTION

Figure 1A:
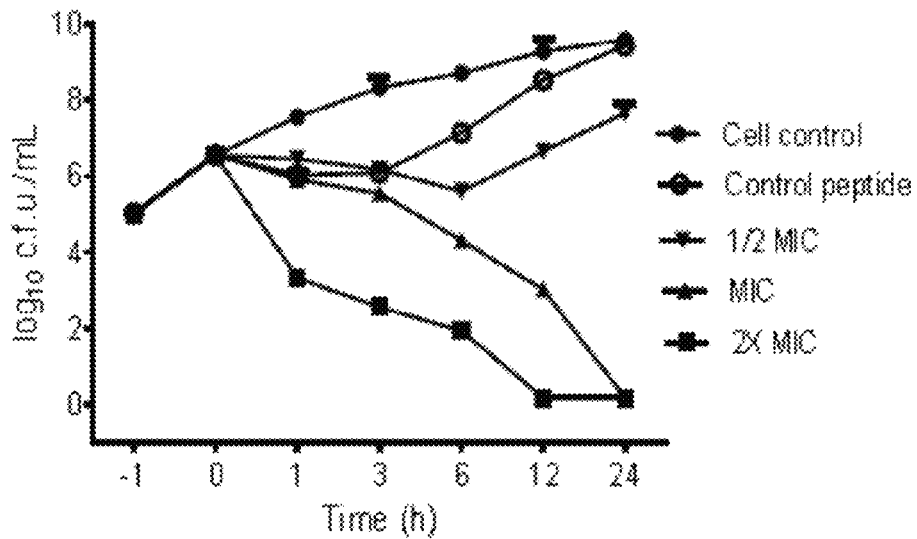
FIG. 1A shows the bactericidal curves of Epi-1 (½, 1, and 2 MIC) against *H. pylori* (ATCC 43504); wherein the control peptide and cells alone were employed as controls; and the samples were collected at 1, 3, 6, 12, and 24 hr post-exposure and colony counts were determined. Each value represents the mean±SEM.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The term "gastric ulcer" as used herein refers to a peptic ulcer disease (PUD), also known as duodenal ulcer, peptic ulcer, stomach ulcer. Gastric ulcer is a sore in the lining of the stomach or duodenum, the first part of the small intestines, accompanying with the most common symptom, a burning stomach pain. In most cases, gastric ulcers are caused by an infection of *Helicobacter pylori* (*H. pylori*).

The term "a functional derivate, fragment or variant thereof" as used herein refers to a derivate, fragment or variant of the peptide that maintains same or similar activity, and exhibits same or similar properties.

The term "therapeutically effective amount" as used herein refers to an amount of a drug or pharmaceutical agent which, as compared to a corresponding subject who has not received such amount, results in an effect in treatment or healing of a disease, disorder, or side effect, or a decrease in the rate of advancement of a disease or disorder. The term also includes within its scope amounts effective to enhance normal physiological function.

The term "pharmaceutically acceptable carrier" as used herein refers to a carrier, diluent, or excipient that is pharmaceutically acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation.

Antimicrobial Peptides (AMPs)

Cationic gene-encoded host defense peptides (HDP) are nature's most diverse and lavish class of antibiotics. Most higher organisms harness these peptides as part of their innate immune system. A subclass of HDP, known as antimicrobial peptides (AMP), exert direct antimicrobial activity. Antimicrobial peptides (AMPs) are part of the host defense system of a wide range of invertebrates, plants, and animals (Lee et al., A helix-PXXP-helix peptide with antibacterial activity without cytotoxicity against MDRPA-infected mice. Biomaterials. 2014; 35:1025-1039; Wimley & Hristova, Antimicrobial peptides: successes, challenges and unanswered questions. The Journal of membrane biology. 2011; 239:27-34). AMPs typically show potent antimicrobial activity against a broad range of bacteria, virus, fungi, and protozoans. The key features of AMPs are that they are short, amphipathic, and cationic, they possess rapid killing ability, and they target the membrane and internal components of the cell (Brogden, Antimicrobial peptides: pore formers or metabolic inhibitors in bacteria, Nature reviews Microbiology. 2005; 3:238-250; Yount &Yeaman, Immunocontinuum: perspectives in antimicrobial peptide mechanisms of action and resistance. Protein and peptide letters. 2005; 12:49-67; Yeaman & Yount, Mechanisms of antimicrobial peptide action and resistance. Pharmacological reviews. 2003; 55:27-55; Hancock & Scott, The role of antimicrobial peptides in animal defenses. Proceedings of the National Academy of Sciences of the United States of America. 2000; 97:8856-8861).

Epinecidin-1 (Epi-1)

The gene encoding the AMP epinecidin-1 (Epi-1) from a cDNA and genomic DNA library of the grouper (*Epinephelus coioides*) was isolated by the inventors. Structurally, Epi-1 is similar to pleurocidin, a protein of the winter flounder (*Pleuronectes americanus*) (Pan et al., Gene expression and localization of the epinecidin-1 antimicrobial peptide in the grouper (*Epinephelus coioides*), and its role in protecting fish against pathogenic infection. DNA and cell biology. 2007; 26:403-413.16; Lin et al., Epinecidin-1, an antimicrobial peptide from fish (*Epinephelus coioides*) which has an antitumor effect like lytic peptides in human fibrosarcoma cells. Peptides. 2009; 30:283-290). It was subsequently reported that Epi-1 acted by inducing direct lysis of bacterial cell membranes, and by causing bacterial clearance through host immunomodulation (Lee et al., The antimicrobial peptide, epinecidin-1, mediates secretion of cytokines in the immune response to bacterial infection in mice. Peptides. 2012; 36:100-108; Huang et al., Use of the antimicrobial peptide Epinecidin-1 to protect against MRSA infection in mice with skin injuries. Biomaterials. 2013; 34:10319-10327; Pan et al., Insights into the antibacterial and immunomodulatory functions of the antimicrobial peptide, epinecidin-1, against *Vibrio vulnificus* infection in zebrafish. Fish & shellfish immunology. 2011; 31:1019-1025). Epi-1 also displayed antibacterial activity against Gram positive bacterial strains, as well as antifungal and antiviral activity (Pan et al., In vitro activities of three synthetic peptides derived from epinecidin-1 and an antilipopolysaccharide factor against *Propionibacterium acnes, Candida albicans*, and *Trichomonas vaginalis*. Peptides. 2009; 30:1058-1068; Wang et al., Inactivation of nervous necrosis virus infecting grouper (*Epinephelus coioides*) by epinecidin-1 and hepcidin 1-5 antimicrobial peptides, and downregulation of Mx2 and Mx3 gene expressions. Fish & shellfish immunology. 2010; 28:113-120; Pan et al., Evaluation of the epinecidin-1 peptide as an active ingredient in cleaning solutions against pathogens. Peptides. 2010; 31:1449-1458).

Tilapia Piscidins

Piscidin AMPs are made up of 21~44 residues that possess an amphipathic-helical structure (Maisetta et al., In Vitro Bactericidal Activity of Human β-Defensin 3 against Multidrug-Resistant Nosocomial Strains. Antimicrobial Agents and Chemotherapy 2006; 50:806-809; Winkler et al., Unexpected Challenges in Treating 432 Multidrug-resistant Gram-negative Rods: Resistance to Ceftazidime-Avibactam in Archived Isolates of *Pseudomonas aeruginosa*. Antimicrob Agents Chemother 2014). Five different piscidins, named tilapia piscidins 1~5 (TP1~5), were isolated from Nile tilapia, *Orreochromis niloticus*, and the coding sequences of the five piscidins were determined by the inventors. The complete piscidins coding sequences of TP1, TP 2, TP 3, TP 4 and TP5 were respectively composed of 207, 234, 231, 270, and 195 bases, and each contained a translated region of 68, 77, 76, 89, and 64 amino acids. The antimicrobial and anti-fungal activities of the five piscidins TP1, TP 2, TP 3, TP 4 and TP5 were determined, revealing that these peptides are potent and promising antimicrobial agents with broad spectra of activity. (Peng et al., Five Different Piscidins from Nile Tilapia, *Oreochromis niloticus*: Analysis of Their Expressions and Biological Functions. PLoS ONE 2012; 7(11): e50263). Synthetic piscidin 2 was reported to have fungicidal activity against *Candida albicans, Malassezia furfur*, and *Trichosporon beigelii* in vitro (Khara et al., Anti-mycobacterial activities of synthetic cationic alpha435 helical peptides and their synergism with rifampicin. Biomaterials 2014; 35:2032-8).

According to the invention, it is found that Epi-1 is effective against different *H. pylori* strains; furthermore, the antibacterial activity occurs through membrane permeation via saddle-splay membrane curvature generation. It was demonstrated in the in vivo efficacy studies that the significant decolonization of *H. pylori* through inhibition of Treg cells and other cytokines, were elevated during infection. Therefore, Epi-1 is effective for use as a mono-therapeutic agent to eradicate multi-drug resistant *H. pylori*.

It is also found in the invention that tilapia piscidins exhibit antibacterial activities against *H. pylori* in vitro. Particularly, it was demonstrated that TP4 had the most potent activity, and was active against a spectrum of strains, while being remarkably stable at low pH. It was also evidenced that TP4 had multiple modes of action, including direct membrane disruption and immunomodulation of the host immune system. It is concluded that (i) TP4 exerts its antimicrobial effects against *H. pylori* via disrupting the membrane via membrane micellization; (ii) the vulnerability of clinical isolates to TP4 is not linked with preexisting resistance to antibiotics; (iii) TP4 acts in a synergistic manner with conventional antibiotics; and (iv) TP4 clears *H. pylori* infection by selectively modulating the host adaptive immune responses against persistent colonization in gastric tissue; and. Collectively. Therefore, TP4 is also effective for use as a therapeutic agent against multidrug resistant *H. pylori*.

Accordingly, the invention provides a method for treating a gastric ulcer comprising administering a subject in need thereof with a therapeutically effective amount of an antimicrobial peptide, a functional derivate, fragment or variant thereof.

On the other hand, the invention provides a method for preventing or treating an infection of *H. pylori*, particularly multidrug resistant *H. pylori*, comprising administering a subject in need thereof with a therapeutically effective amount of an antimicrobial peptide, a functional derivate, fragment or variant thereof.

In the invention, the antimicrobial peptide is selected from the group consisting of Epi-1, TPs and combination thereof. In one particular example, the TP is TP4.

In one yet aspect, the present invention provides a composition or a pharmaceutical composition for preventing or treating an infection of *H. pylori*, particularly multidrug resistant *H. pylori*, comprising a therapeutically effective amount of an antimicrobial peptide, a functional derivate, fragment or variant thereof, in which the antimicrobial peptide is selected from the group consisting of Epi-1, TPs and combination thereof.

On the other hand, the present invention provides a use of an antimicrobial peptide, a functional derivate, fragment or variant thereof, for manufacturing a medicament for treating a gastric ulcer, or preventing or treating an infection of *H. pylori*, particularly multidrug resistant *H. pylori*.

In the invention, the composition or pharmaceutical composition may be formulated using any standard technology or commonly used methods known to those skilled in the art.

For use in therapy, therapeutically effective amounts of the peptide, or functional variant thereof, may be formulated as a pharmaceutical composition for administration. Accordingly, the invention further provides a pharmaceutical composition comprising a therapeutically effective amount of the peptide or a functional derivate, fragment or variant thereof, together with one or more pharmaceutically acceptable carriers.

According to the invention, the pharmaceutical composition may be adapted for administration by any appropriate route, including but not limited to topical, rectal, nasal, vaginal, oral or parenteral route. In one particular example of the invention, the pharmaceutical composition is formulated for intratumoral administration. Such formulations may be prepared by any method known in the art of pharmacy. One example of the invention is a pharmaceutical composition in the form an injectant.

The present invention will now be described more specifically with reference to the following examples, which are provided for the purpose of demonstration rather than limitation.

EXAMPLES

Example 1

Study on Epi-1

1.1 Materials and Methods 1.1.1 Bacterial Strains, Growth Conditions, and Antimicrobial Peptide Synthesis

*H. pylori* strains were obtained from the American Type Culture Collection (ATCC 43504, 700392, and 51653), and MDR clinical isolate was provided by Dr. Chang-Jer Wu (Department of Food Science, Nation Taiwan Ocean University). The strains were identified on the basis of colony appearance, Gram staining, and positive reactions in the rapid urease test. *H. pylori* strains were revived and cultured on brain heart infusion (BHI) agar (Difco Laboratories, Detroit, Mich.) supplemented with 10% sheep blood (Invitrogen, NY). The plates were incubated for 24 hr at 37° C. in a microaerophilic atmosphere (Anaeropack-Anaero, Mitsubishi, Japan). TH2-3 (QSHLSLCRWCCNCCR-SNKGC) (SEQ ID NO: 1), TP3 (FIHHIIGG-LFSVGKHIHSLIHGH) (SEQ ID NO: 2), Epi-1 (GFIFHIIKGLFHAGKMIHGLV) (SEQ ID NO: 3), GE-33 (GFFALIPKIISSPL-FKTLL-SAVGSALSSSGGQE) (SEQ ID NO: 4), and Chrysophsin (FFGWLIKGAIH-AGKAIHGLIHRRRH) (SEQ ID NO: 5) were (i) synthesized by solid-phase peptide synthesis, (ii) purified by reverse-phase high-performance liquid chromatography to a grade of >95%, and (iii) lyophilized by GL Biochemistry (Shanghai, China)[24]. The lyophilized synthetic peptides were reconstituted in PBS to generate working stocks prior to each experiment.

1.1.2 In vitro *H. pylori* Growth Inhibition Assay

Antibacterial activities were evaluated by examining MIC; determined using the micro dilution assay in sterilized 96-well plates in a final volume of 200 µl as follows. Bacterial inocula of 0.1 OD were prepared and diluted 1000 fold in BHI broth, and 180 µl aliquots were added to each well. Working standards of antimicrobial peptides (Epi-1, TH2-3, SALF, GE-33, or Chrysophsin-1) were prepared (0.9-50 µg/mL) prior to the experiment; 20 µL of AMP solution were added to each well. PBS was used as a control. The plates were incubated overnight at 37° C. in a microaerophilic atmosphere. Growth under standard conditions was determined by optical density measurements at 600 nm. The MIC was considered the lowest peptide concentration that resulted in no increase in optical density after 24 hr of incubation.

1.1.3 Time-kill Kinetics

Overnight bacterial cultures were diluted to 0.1 OD, and culture inocula were incubated in the presence or absence of Epi-1 (at 0.5, 1, or 2-fold MIC) without shaking at 37° C. for up to 24 hr under microaerobic conditions. Aliquots were aspirated at 1, 3 6, 12, and 24 hr post-exposure, and the number of viable bacteria (CFU) were determined.

1.1.4 Dose-dependent Efficacy of Epi-1 and Antibiotics

The antibacterial activity of Epi-1 against *H. pylori* was compared to that of AMX, MTZ and CLR, using Turbidity fall assay. Briefly, *H. pylori* (0.5 OD) were exposed to Epi-1 at various concentrations (0.19-25 µg) or antibiotics (0.02-2 µg). The treated groups were incubated at 37° C. overnight under microaerobic conditions, and then optical density (OD 600) was recorded and plotted.

1.1.5 Examination of *H. pylori* Membrane Integrity with 1-N-phenylnaphthylamine (NPN)-uptake Assay Briefly, *H. pylori* culture inoculae (0.5 OD) were incubated with various concentrations of Epi-1 for 6 hr at 37° C. under microaerobic conditions. Cultures were then pelleted, and 22 µg/ml NPN reagent was added to the pellets to a final volume of 250 µl. Finally, fluorescence was recorded. Increases in fluorescence were considered to be a correlate of *H. pylori* membrane potential and permeation. All assays were performed at room temperature.

1.1.6 Zeta-potential Measurements

*H. pylori* was cultured in blood agar or broth to $3\times10^7$ cfu/mL, in order to acquire sufficiently high count rates. Measurements were made at 37° C. in the presence or absence of Epi-1, and the mean of 15 measurements (120 runs each) was determined. Zeta-potential values were obtained by phase analysis light scattering (PALS) in a Zetasizer Nano ZS (Malvern Instruments, Malvern, UK), using disposable zeta cells with gold electrodes.

1.1.7 Transmission Electron Microscopy Studies

Transmission electron microscopy was used to examine Epi-1 induced morphological changes of *H. pylori*. The samples were fixed and processed as previously described [28]. All samples were examined with an FEI Tecnai G2 F20 S-TWIN transmission electron microscope (FEI Company, Hillsboro, Oreg.) operating at an accelerating voltage of 80 kV. Images were recorded with a charge-coupled device camera at various magnifications.

1.1.8 Determination of the in vivo Efficacy of Epi-1 in a Mouse Model of *H. pylori* Infection Six-week-old C3H/HeN male mice were used for this study; mice were obtained from BioLASCO Tawian, co., Ltd., and housed at the Laboratory Animal Facility, National Taiwan Ocean University, Keelung, Taiwan. Animals were provided with food and water ad libitum. All animal protocols with reference number 96025 were approved by the Institutional Animal Care and Use Committee (IACUC) of the College of Science, National Taiwan Ocean University. Six week-old adult mice were randomly divided into three groups of six mice each. Overnight *H. pylori* cultures were harvested from blood agar. Mice were challenged with *H. pylori* (~1×10$^9$ cells) via intragastric gavage; mice received a second dose of the same number of cells after a 24 hr interval. Following colonization on day 9 onwards, the animals were treated with Epi-1 (250 µg/animal)/10MIC of PPI-Triple therapy antibiotics (Proton pump inhibitor, amoxicillin, clarithromycin, and metronidazole) for 14 days; the control group received an equivalent volume of PBS. After treatment mice were euthanized, the stomach and spleen tissue were harvested; the spleen was processed for T cell subset population analysis by flow cytometry. The harvested stomach was cut into two halves, one half for histology and the other half for bacterial enumeration and other analyses. Suspensions were serially diluted and spread onto *H. pylori* selective EYE-agar plates in duplicate, and then incubated for 24 hr. Total colony forming units (CFU) were counted and expressed as CFU/g stomach.

1.1.9 Histological Analysis of Gastric Tissue Sections

Gastric tissue biopsies were fixed in buffered paraffin and embedded in paraffin wax. A section of about 5 µm was stained with hematoxylin and eosin to analyze tissue inflammation. For immunofluorescence staining against *H. pylori*, tissue slides were deparaffinized with xylene and alcohol, and then rehydrated in water. Antigen retrieval was performed by incubating sections in a 10 mM sodium citrate buffer at pH 6.0 in a pressure cooker for 10 min. After washing in PBS, the tissue section was incubated first with rabbit polyclonal *H. pylori* antibody (1:200) (GeneTex, Taiwan) and then with FITC-labeled goat anti-rabbit secondary antibody (1:500). The labeled sections were then counter stained with DAPI. The sections were observed at different magnifications under light microscopy. Tissues were evaluated as described previously. For Giemsa staining, the slides were stained for 2-5 minutes and washed with PBS to remove excess stain. Slides were fixed, and then observed under light microscopy. The tissues were evaluated as described previously.

1.1.10 Analysis of Splenic T Cell Subset Populations by Flow Cytometry

Mice spleens were harvested from euthanized mice and placed in RPMI media. Spleens were minced and passed through a 100µ size mesh screen at room temperature, before being centrifuged at 1500 rpm for 5 min. The resulting pellet was resuspended in 3 ml of RBC lysis buffer, and incubated for 5 min at room temperature (RT) with regular tapping; the reaction was halted by diluting the buffer with RPMI media. The mixture was centrifuged, and the pellet was resuspended in 1 ml RPMI media with 1-2% FBS. The resulting single-cell suspension was aliquoted into flow cytometry tubes (100 µl/tube). One microliter of fluorescently-labeled monoclonal antibody (CD4, Th17, Treg cells) was added to each tube, and the volume was made up to 500 µl with PBS. The tubes were covered with foil and incubated in the dark for 1 hr at room temperature. Finally, the samples were analyzed using a BD FACSCanto flow cytometer, and the percentages of each cell subset were recorded.

1.1.11 Gene Expression Analysis

Total RNA from mouse gastric tissue was isolated using the High Pure RNA Tissue Kit, according to the recommendations of the manufacturer (Roche, USA). For cytokine mRNA quantification, 5 µg of total RNA was converted into cDNA using a high capacity cDNA archive kit (Invitrogen). Levels of interleukin IL-6, IL-10, IL-17, tumor necrosis factor alpha (TNF-α), and Foxp3 mRNA were measured by Q-PCR using TaqMan gene expression assays for use in the A CFX Connect™ Real-Time PCR Detection System (Bio-Rad). Transcript levels were normalized to mRNA of the endogenous control, glyceraldehyde-3-phosphate dehydrogenase (GAPDH), and expressed as the fold change compared to samples from control mice using the Comparative CT method (Bio-Rad).

1.1.12 Toxicity Evaluation

Oral Toxicity:

Acute oral toxicity was assessed in mice with 6 animals per group, by single oral administration of Epi-1 at 125 mg/kg body weight [37, 38]. Animals were placed under observation for about 48 hr. The mortality, morbidity rate, and clinical signs were recorded.

Sub-acute Oral Toxicity:

Sub-acute oral toxicity was assessed with over a test period of 14 days in which mice were given 600 µg/mouse/day [39]. During the study period, animals were observed daily for clinical signs and mortality. After the test period, animals were allowed to recover, and were observed for the development of other clinical abnormalities for 14 days.

Dermal Toxicity:

Dermal toxicity was assessed in Balb/c mice, through administering daily doses of Epi-1 (2.5 mg/animal) for 7 days [40, 41]. Animals were kept under observation for a minimum of 48 h. Skin abnormalities were recorded.

Eye Irritation Test in Rabbits:

This study used healthy young adults of the New Zealand white albino rabbit breed. One eye of each animal served as a negative control, while the other eye was treated with Epi-1 (1 mg/kg) for 7 days; positive control rabbits were treated with 0.1% SDS. The eyes were examined on days 1, 3, 5, and 7, and then allowed to recover until day 14; at this time, clinical observation scores were recorded, and grades assigned for ocular reactions observed during each examination.

1.2 Results 1.2.1 Antibacterial Effects of Epinecidin-1 against *H. pylori*

Five different cationic peptides for activity against *H. pylori* strain G27 were initially screened. The names and sequences of these peptides are given in Table 1.

TABLE 1

Antimicrobial activity of different antimicrobial peptide sequences against antibiotic-sensitive and resistant clinical isolate *Helicobacter pylori* strains.
MIC (µg/mL)[a]

| | | *H. pylori* strains | | | |
|---|---|---|---|---|---|
| Antimicrobial | | ATCC | | | Isolate |
| Peptides | Sequences | 43504 | 700392 | 43629 | CI-HP028[b] |
| TH2-3[42] | QSHLSLCRWCCNCCRSNKGC | NE[c] | NE | NE | NE |
| TP3 [43] | FIHHIIGGLFSVGKHIHSLIHGH | NE | NE | NE | NE |

TABLE 1-continued

Antimicrobial activity of different antimicrobial peptide sequences against antibiotic-sensitive and resistant clinical isolate Helicobacter pylori strains.
MIC (µg/mL)[a]

| Antimicrobial Peptides | Sequences | H. pylori strains | | | |
|---|---|---|---|---|---|
| | | ATCC | | | Isolate |
| | | 43504 | 700392 | 43629 | CI-HP028[b] |
| Epi-1[19] | GFIFHIIKGLFHAGKMIHGLV | 8-12* | 8-12* | 8-12* | 8-12* |
| Pardaxin[44] | GFFALIPKIISSPLFKTLLSAVGSALSSSGGQE | >25 | >25 | >25 | >25 |
| chrysophsin-1[45] | FFGWLIKGAIHAGKAIHGLIHRRRH | NE | NE | NE | NE |

[a]The minimum inhibitory concentration (100.1% survival).
[b]CI-HP028: Clinical isolate,
[c]NE: No effect
*All H. pylori strains are sensitive to Epi-1 (p < 0.001)

Concentrations of each peptide ranging from 0.4 to 100 µg were initially screened. One of the five peptides examined, Epi-1, exhibited strong growth-inhibitory and/or bactericidal effects against sensitive and multidrug resistant *H. pylori* strains (ATCC 43504, 51653, 700392, and antibiotic resistant clinical isolate CI-HC-028). The rate at which antimicrobial agents exert antibacterial activity is particularly important when considering probable therapy for *H. pylori* infection, due to the relatively rapid clearance of gastric contents, which ultimately reduce the exposure time of *H. pylori* to orally ingested antimicrobial agents. FIG. 1A shows dose- and time-dependent efficacy of Epi-1 against *H. pylori*; 2× and 1×MIC Epi-1 decreased *H. pylori* by 90% at 1 and 12 hr postexposure, respectively. At 0.5×MIC, bacterial counts initially decreased, but increased exponentially after 6hr post-exposure. These data indicate that the Epi-1 bactericidal effect against antibiotic-sensitive and -resistant strains of *H. pylori* is dose- and time-dependent with a minimum bactericidal concentration (MBC) of 12.5-25 µg.

Figure 1B:
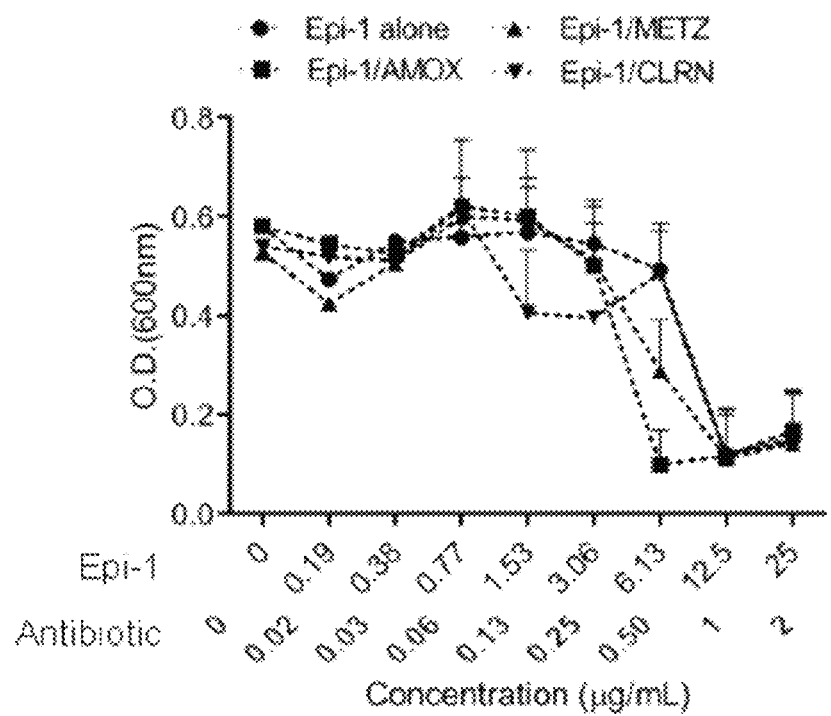
FIG. 1B shows the results of the turbidity fall assay on the synergistic effects of Epi-1 and antibiotics, including amoxicillin (AMOX), metronidazole (METZ), and clarithromycin (CLRN) against resistant *H. pylori*; wherein the data shown are means±SEM of two independent experiments.

1.2.2 Turbidity Fall Assay: Comparison of Epi-1 and Antibiotic Activity against a Resistant Clinical Isolate Any new drug should exhibit stronger or at least comparable efficacy to antibiotics currently used in treatment. We examined the dose-dependent antibacterial activity of Epi-1 combined with antibiotics amoxicillin (AMOX), METZ (metronidazole), and CLRN (clarithromycin), which are used in *H. pylori* therapy (FIG. 1B). Epi-1 exhibited synergic effects with AMOX, METZ, and CLRN, significantly decreasing the MIC. Epi-1 alone or in combination with antibiotics is superior to antibiotics alone.

1.2.3 Epi-1 Induces *H. pylori* Membrane Permeabilization

Figure 2A:
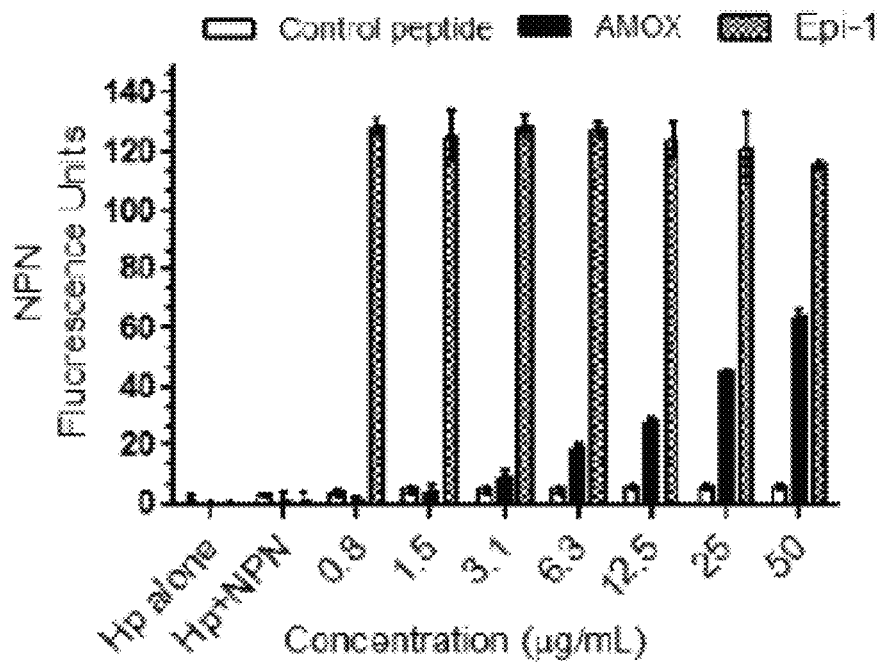
FIG. 2A showing the dose-dependent effect of Epi-1 on permeabilization of the *H. pylori* membrane, which was examined based on uptake of a fluorescent probe, 1-N-phenylnaphthylamine (NPN); wherein approximately $5 \times 10^6$ *H. pylori* (Hp) cells were exposed to the indicated concentrations of Epi-1 and amoxicillin (AMOX) for 6 h. Cells alone or with NPN were used as controls; and the emitted NPN fluorescence intensity was recorded as a correlate of membrane permeation.

Antibiotics inhibit cell wall synthesis only at high concentrations, due to the development of resistance mechanisms in pathogenic bacteria. Antimicrobial peptides act through numerous mechanisms, but principally by disrupting the membrane of the target bacteria, Membrane disruption was examined by measuring uptake of NPN fluorescence. Exposure of *H. pylori* to sub-MIC concentrations of Epi-1 for 2 hr resulted in rapid increases in fluorescence; amoxicillin resulted in smaller and dose-dependent increases (FIG. 2A). The fluorescence intensity was saturated at higher concentrations of Epi-1, which correlate with dose-dependent kinetics of Epi-1. Overall, these data evidence that Epi-1 causes membrane disruption.

1.2.4 Effect of Zeta Potential Measurements on *H. pylori*

Figure 2B:
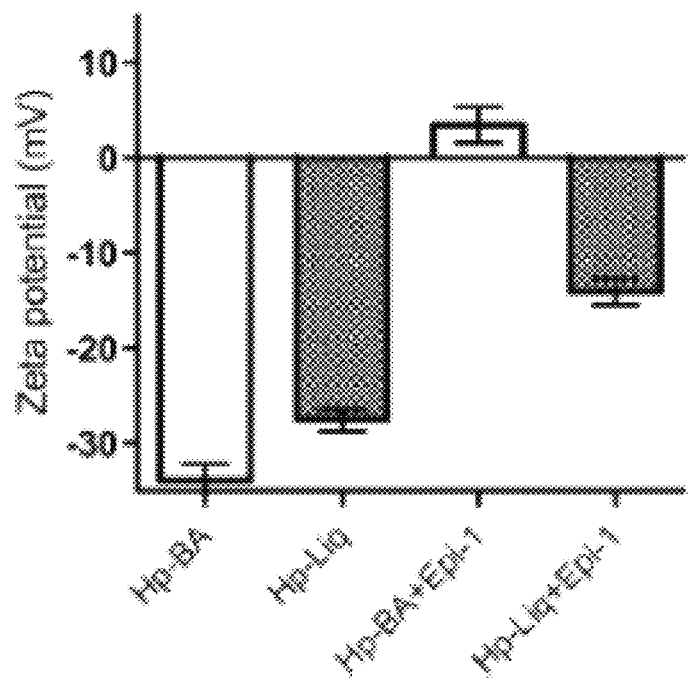
FIG. 2B shows the effect of Epi-1on the zeta-potential of *H. pylori* (grown on blood agar (BA): white bars; grown in liquid culture (Liq): hatched bars; grown in the presence of Epi-1: +Epi-1); wherein the data shown are means±SEM of two independent experiments.

To confirm that Epi-1 can interact with, bind, and disrupt the *H. pylori* membrane, zeta-potential was measured to examine surface charge. As shown in FIG. 2B, *H. pylori* cultured on blood agar or in broth culture presented with a negative charge (−33.87±0.75 mV and −27.5±0.75 mV, respectively). By adding Epi-1 to either culture, the zeta potential became less negative (+3.52 and −14.03±0.75 mV, respectively). These data suggest that Epi-1 can interact with the negative surface of *H. pylori*, causing drastic membrane permeation; furthermore, these data are consistent with the NPN uptake findings. Overall, the results reveal potential binding of Epi-1 to the *H. pylori* surface, which may cause a membrane disruption cascade.

Figure 3:
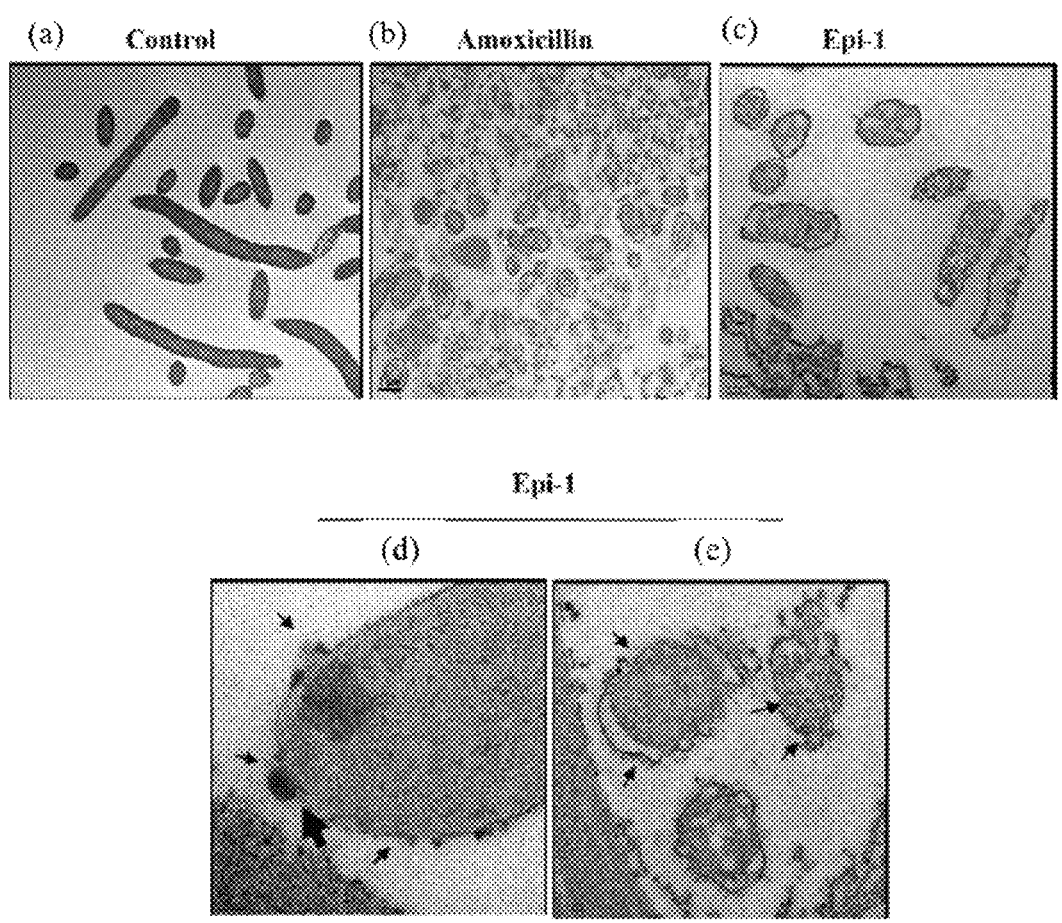
FIG. 3 shows the transmission electron micrographs of the morphological changes in *H. pylori* after exposure to Epi-1 wherein the cells were examined with a transmission electron microscope after glutaraldehyde fixation.

1.2.5 Transmission Electron Micrography Reveals that Epi-1 Induces Saddle Splay Membrane Curvature Generation As shown in FIG. 3, (a) untreated cells show normal morphology, with distinct, intact inner and outer membranes, and a thin, uniform periplasmic space. (b) amoxicillin-treated *H. pylori* cells exhibited a low percentage of coccoid morphology; these enlarged cells were typified by clear separation of the plasma membrane from the outer membrane. Additionally, some cells exhibited a complete loss of cytoplasmic content; these lysed cells had membranes similar to those previously described for *H. pylori* ghost cells [45]. (c) *H. pylori* samples that were exposed to Epi-1 showed a significantly altered morphological phenotype as compared to control cells. Most of the cells of the Epi-1-treated cells appeared as ghost cells. Epi-1 treatment selectively induced saddle-splay membrane curvature (non-zero curvature) in *H. pylori* membranes; induction of such curvature is a necessary condition for several processes, including pore formation, blebbing, budding, and vesicularization (d)-(e), which are involved in destabilizing membranes. (d) shows vesicular budding and blebbing of the membrane upon exposure to Epi-1. Excessive budding and blebbing lead to membrane lysis and release of cellular constituents through the introduced pores (arrows in (e)). Cell lysis and loosening of the outer membrane are evident in the micrographs.

1.2.6 In vivo Efficacy of Epi-1 against *H. pylori* Infection in a Mouse Model

Figure 4:
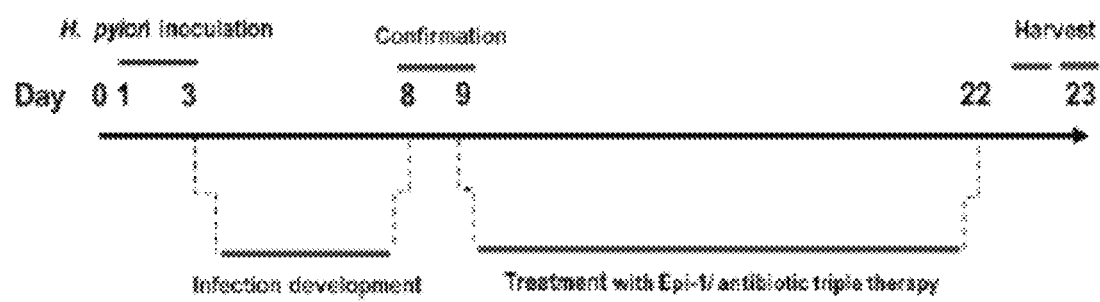
FIG. 4 provides the scheme for examining efficacy of Epi-1 in mouse models of *H. pylori* infection; wherein the inocula ($1 \times 10^9$ cfu/animal) were orally administered on days 1 and 3; colonization by bacteria was confirmed on day 9. From day 9 onwards, infected mice were given daily doses of 250 μg Epi-1 or 10×MIC of antibiotic quadruple therapy (PPI (proton pump inhibitor), amoxicillin, clarithromycin, and metronidazole) for two weeks; animals were sacrificed on day 23 and total viable counts were recorded.
Figure 5A:
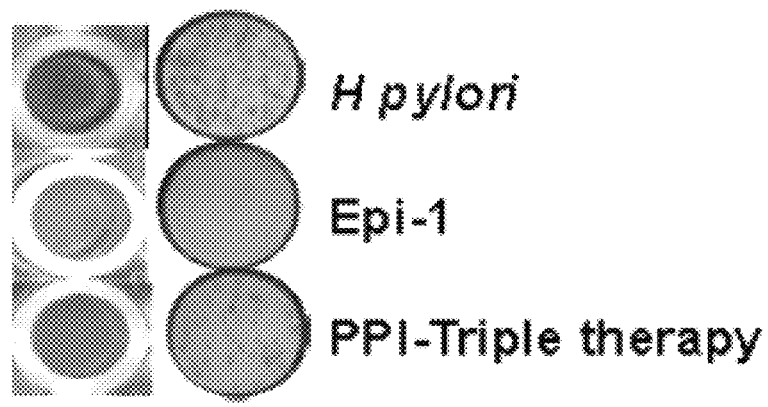
FIG. 5A provides the results of the rapid urease test for *H. pylori* identification in gastric tissue lysate; the left, from top shows the group of untreated; the group of Epi-1-treated cells; the group of triple therapy-treated cells; wherein the pink colonies represented positive for *H. pylori* infection; and the right shows the cultured selection media plates.
Figure 5B:
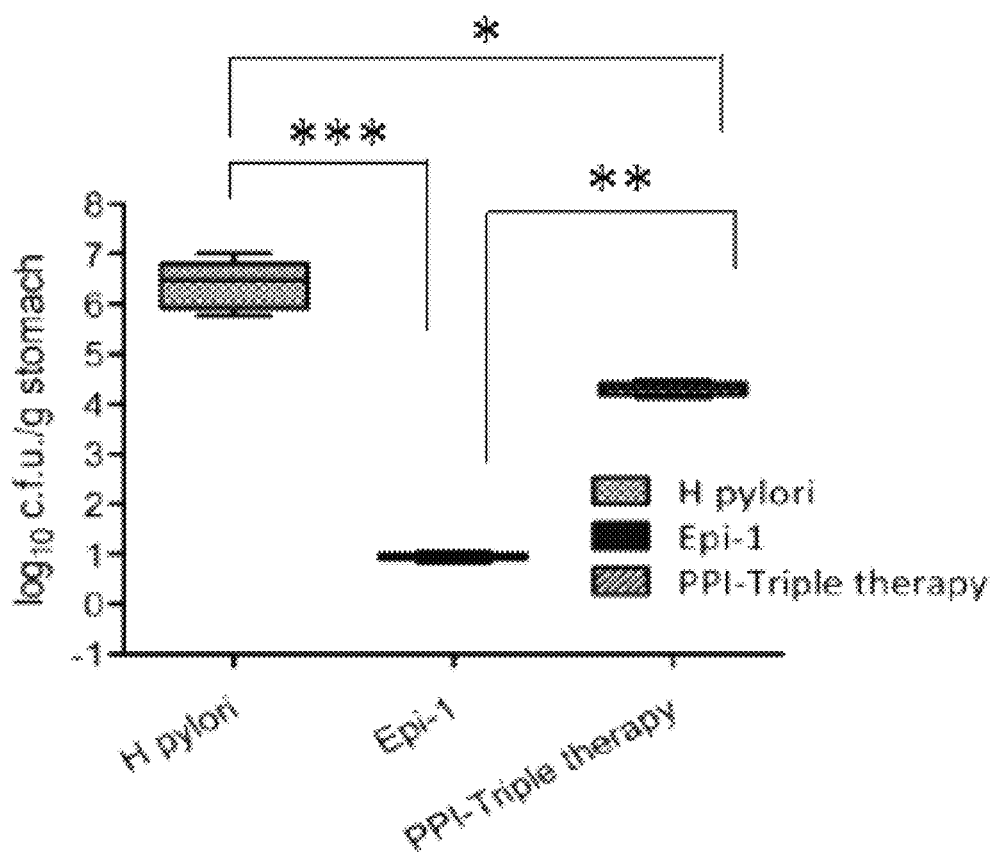
FIG. 5B provides the quantification of bacterial burden in the stomach of untreated *H. pylori*-infected mice, infected mice treated with Epi-1, or infected mice treated with triple therapy (n=6 per group); wherein bars represent means±SEM. *$P<0.05$, $P<0.001$, $P<0.0001$.

Based on our strong in vitro data, we next sought to evaluate the in vivo therapeutic efficacy of Epi-1 against *H. pylori* in a model of infection (scheme shown in FIG. 4). We infected C3H/HeN mice with *H. pylori* inocula ($1 \times 10^9$ CFU) on day 1, and re-challenged mice on day 3 with the same dose. Colonization was confirmed at 8 days post-infection. From day 9, mice were given daily doses of Epi-1 (250 µg)

or PPI-Triple therapy (10×MIC) for two weeks. The mice were then sacrificed, and organs were harvested. The stomach lysates were prepared for various biochemical and histopathological tests. Infection control and antibiotic groups tested positive for *H. pylori* in the rapid urease test (FIG. 5A). Therapeutic efficacy was evaluated by comparing *H. pylori* counts in mouse gastric tissue between untreated and triple therapy groups (FIG. 5B). After the study period, $5\times10^6$ CFU *H. pylori*/g stomach tissue was observed for the untreated group, which was reduced by 2 orders of magnitude ($4\times10^4$ CFU/g) in the PPI-Triple therapy group. Epi-1 treatment resulted in 100% clearance (*H. pylori* could not be detected through urease test, PCR, Western blot, or selective agar plating), suggesting that Epi-1 is an effective monotherapeutic agent against *H. pylori* infection.

1.2.7 Immunofluorescence Detection of *H. pylori* Infection in Gastric Tissue

Figure 6:
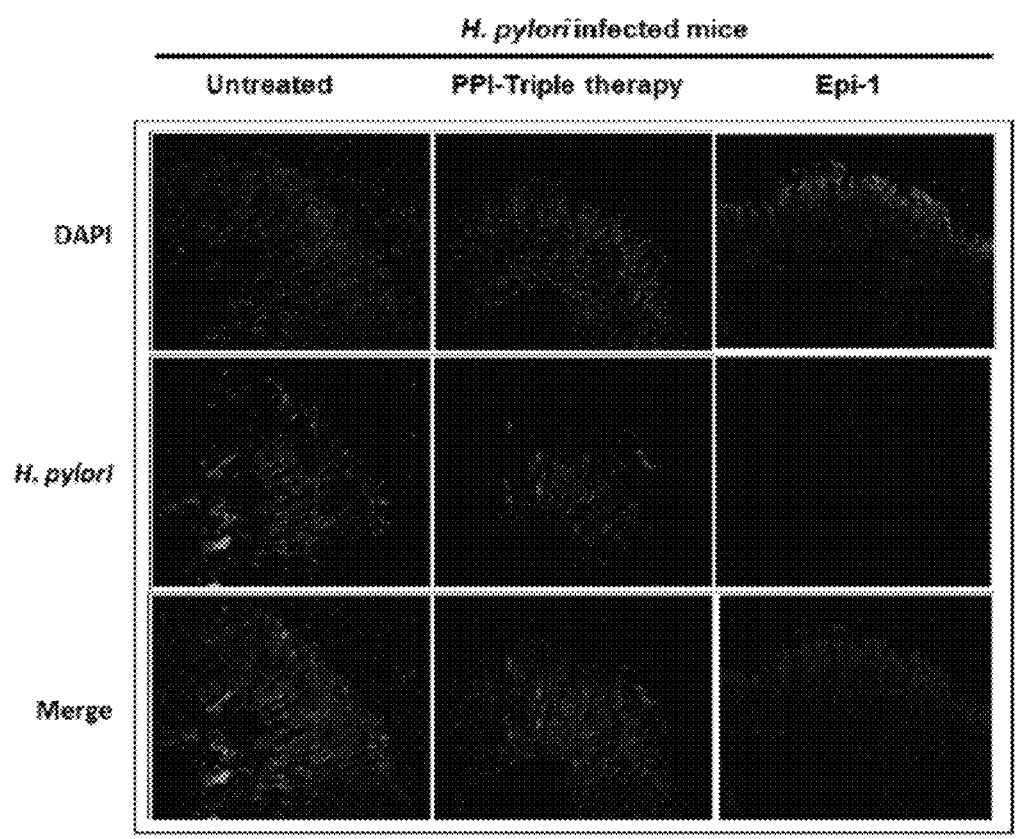
FIG. 6 shows the immunofluorescence of gastric tissue sections of *H. pylori*-infected mice untreated/treated with PPI-triple therapy antibiotics or Epi-1. The fluorescence indicates the presence of *H. pylori* (magnifications 200×).

The immunofluorescence staining to detect *H. pylori* in gastric tissue sections was subsequently used. As shown in FIG. 6, untreated mice infected with *H. pylori* exhibited green fluorescence, indicative of bacteria at the surface lining of the stomach and towards muscularis mucosae. *H. pylori* were also present in the glandular lumina, and penetrated deeply into the gastric glands. PPI-Triple therapy (antibiotic) decreased fluorescence, but failed to eradicate bacteria from the gastric tissues (consistent with *H. pylori* counts. Conversely, fluorescence was not observed in sections from Epi-1 treated groups, indicating significant clearance of *H. pylori* at the tissue level.

1.2.8 Histological Examination for Gastric Inflammation Evaluation

Figure 7:
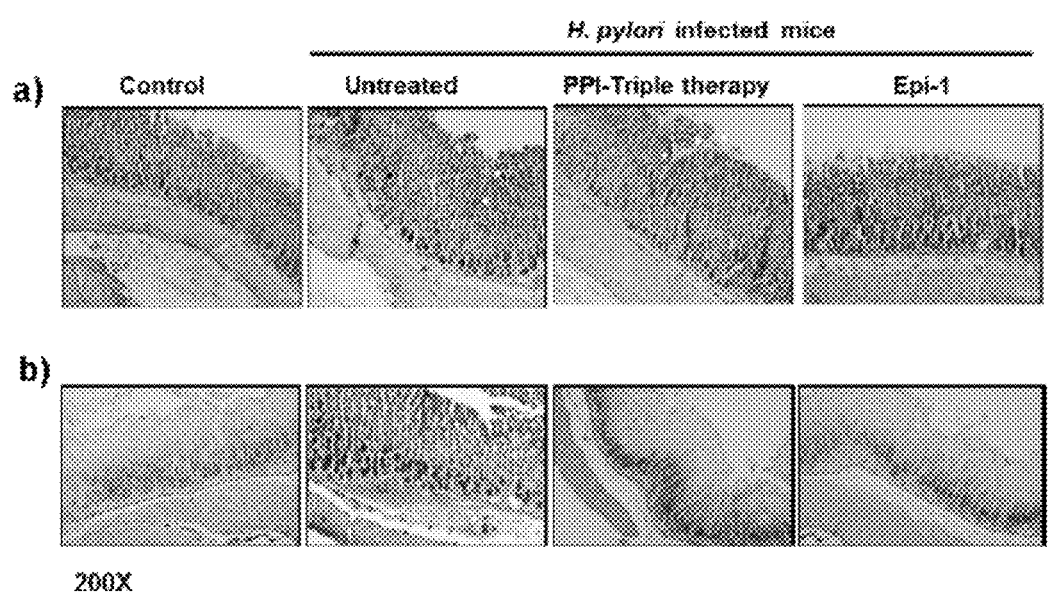
FIG. 7 shows the histological staining analysis of *H. pylori*-infected mice untreated/treated with PPItriple therapy antibiotics or Epi-1. The image (a) shows the HE staining for gastric inflammation scoring during infection and after therapy, and the image (b) shows the Giemsa staining for immune cell infiltration (scale bar: 50 μm).

Gastric tissue sections were stained with hematoxylin-eosin and Giemsa stain for histological examination (FIG. 7). (a) Inflammation was significant in untreated mouse gastric sections; further, the ulcer crater and muscularis mucosae layer was heavily infiltrated with immune cells. (b) These inflammatory cells infiltrated towards the foveolar, chief, and parietal cell region, resulting in superficial damage to the surface epithelium. Such effects were caused by *H. pylori*-mediated modulation of the host immune system during colonization. PPI-Triple therapy did not affect inflammation, while Epi-1 treatment significantly reduced both inflammation and immune cell infiltration at ulcer crater and muscularis mucosae. These data suggest that monotherapeutic doses of Epi-1 restore gastric tissue morphology through significant clearance of *H. pylori*.

Figure 8A:
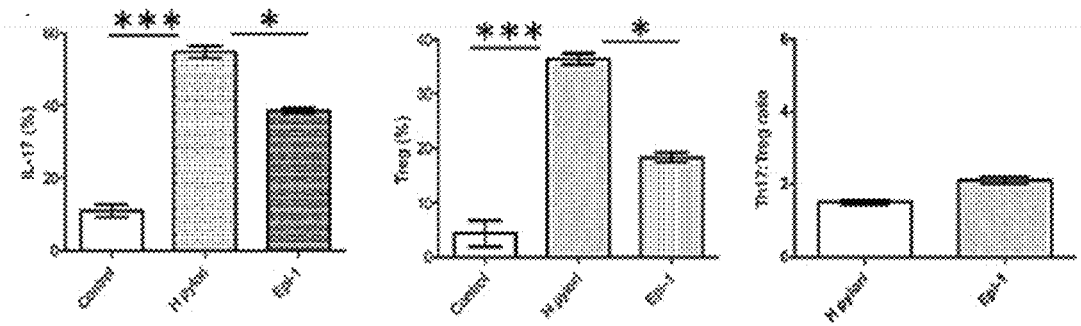
FIG. 8A shows the effect of Epi-1 on *H. pylori*-induced host immune responses (indicated proteins); wherein splenic T subset populations were quantified using fluorescent antibodies against inflammatory and anti-inflammatory T cells. Epi-1 treatment balanced the splenic T cell subset response between inflammatory and anti-inflammatory responses induced by *H. pylori* infection.

1.2.9 Effects of Epi-1 on *H. pylori*-induced Predominance of CD4+Foxp3, Th17 T Cell Subsets in Splenocytes Recent studies have indicated that *H. pylori* infection induces strong regulatory T cell (Treg) polarization against helper T cell immunity to enhance persistent colonization by *H. pylori*; the initial increase in Th17 cells causes inflammation to aid in colonization (FIG. 8A), but a low Th17/Treg ratio is maintained to counter the host immune response. Epi-1 treatment significantly reduced *H. pylori* biased Treg subsets, and moderately decreased Th17 counts; further, Epi-1 restored the Th17/Treg balance (FIG. 8A). This indicates, for the first time, that Epi-1 inhibits *H. pylori*-mediated modulation of host immune responses, possibly resulting in the observed decrease of *H. pylori* colonization. These data correlate with the effects on bacterial burden in gastric tissue shown in FIG. 5B.

Figure 8B:
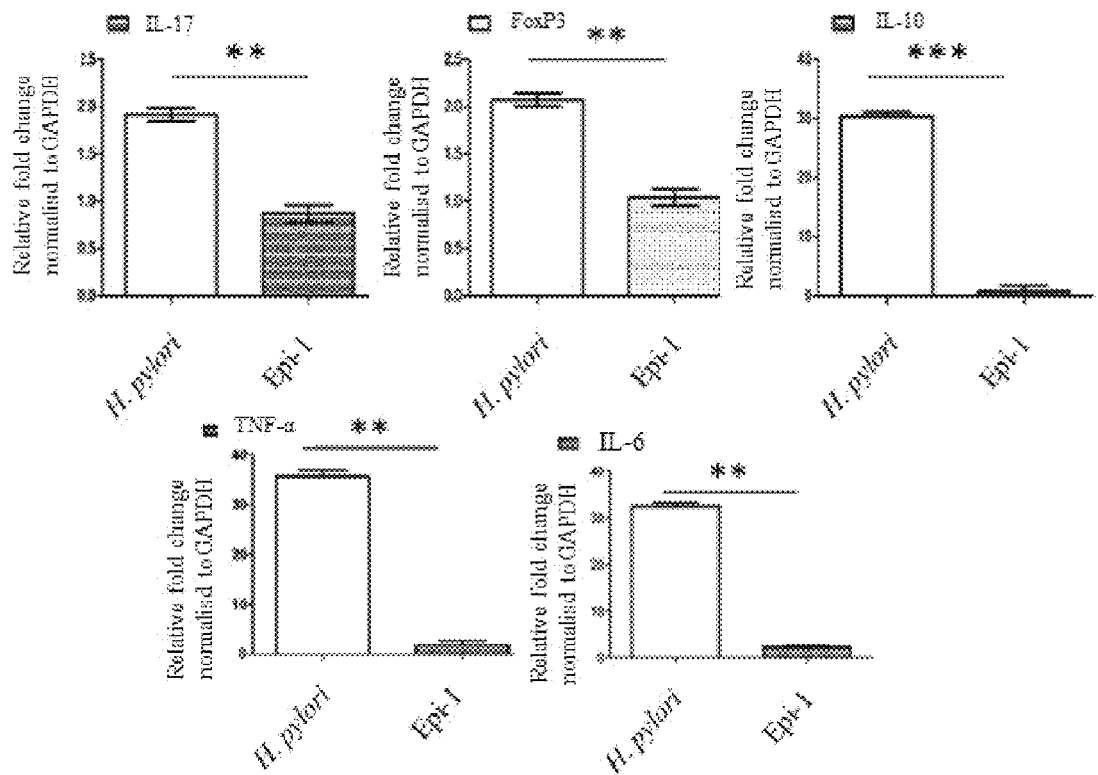
FIG. 8B shows the effects of Epi-1 on expression of the indicated genes regulating inflammatory and antiinflammatory responses in *H. pylori*-infected mice; wherein gastric tissue mRNA was isolated from untreated and treated mice, and mRNA expression was measured by real-time PCR. Figures are means±SEM.
Figure 9:
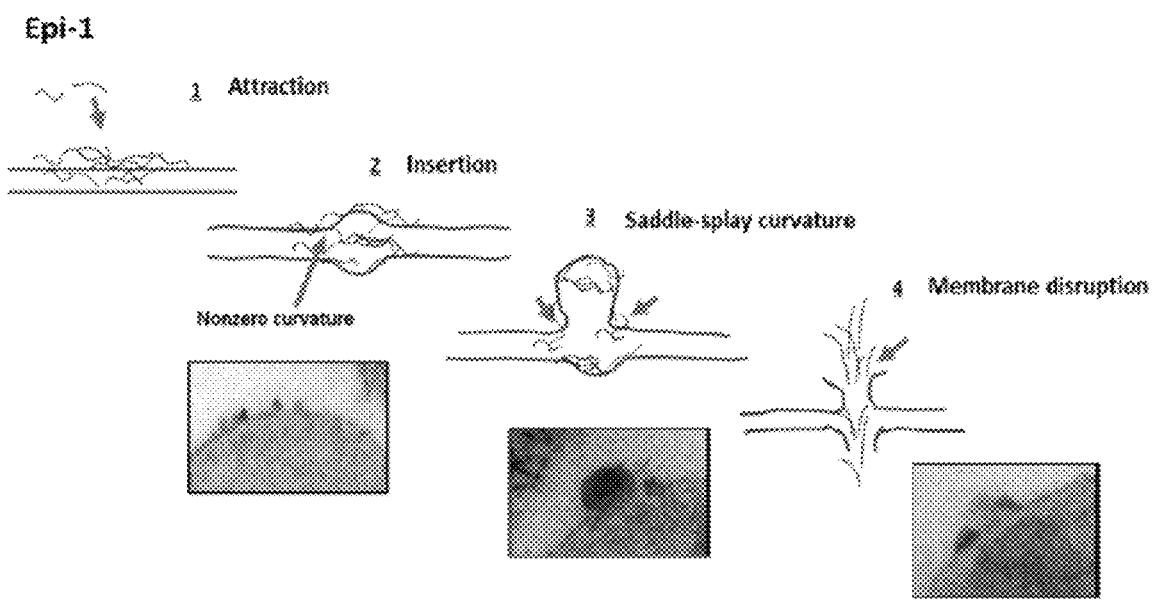
FIG. 9 provides the proposed mechanism of action of Epi-1 against *H. pylori*, including: 1) attraction of Epi-1 onto membrane, 2) insertion/integration into membrane lipid leaflets creating non zero curvature tension among lipid molecules, 3) saddle-splay curvature led to membrane vesicular budding/blebbing, and 4) membrane disruption due to extensive nonzero curvature tension led to destabilized membrane integrity, release of cellular contents caused *H. pylori* death.

1.2.10 Effect of Epi-1 on *H. pylori*-induced Expression of Cytokine mRNA in Gastric Tissue To further evaluate *H. pylori*-induced immune responses in gastric tissue, we performed real time PCR to measure the effect of Epi-1 treatment on mRNA expression levels of genes encoding cytokines and T cell markers in infected mice (FIG. 8B). We report that certain cytokines (Tumor necrosis factor-α, IL-6, IL-10, and IL-17) and the T-cell marker FOXP3 were significantly up-regulated during *H. pylori* infection. IL-10 and IL-17 play major roles in persistent *H. pylori* colonization and gastric inflammation. Epi-1 significantly inhibited expression of IL-10, which plays a key role in Treg cell development; moreover, Epi-1 restored the Th17/Treg balance.

1.2.11 Preclinical Toxicity Evaluation

It was reported that acute and sub-acute oral administration of Epi-1 (at dosages of 125 mg/kg and 600 μg/mice, respectively) did not induce any clinical abnormalities, morbidity, or death in mice. The biochemistry of whole blood was examined: no significant changes were observed in the levels of glutamic oxaloacetic transaminase (GOT), glutamic pyruvic transaminase (GPT), blood urea nitrogen (BUN), creatinine (CRE), total bilirubin (TBIL), or uric acid (UA). Body growth was also normal.

Figure 10A:
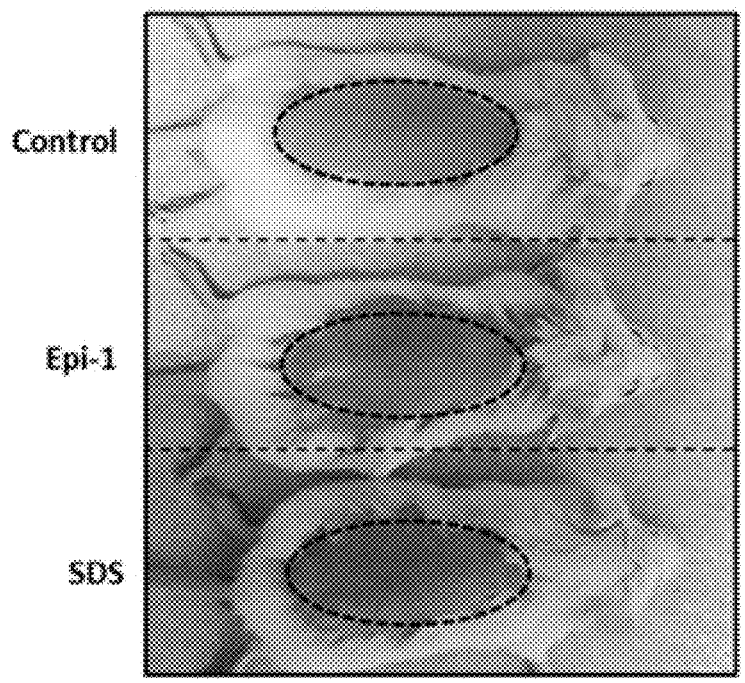
FIGS. 10A and 10B show the results of the toxicity evaluation of EPi-1.

Dermal toxicity tests (application of 2.5 mg Epi-½ cm2 skin surface) did not cause any irritation, lesions, or clinical signs at the applied region, as compared with SDS (positive control). Hair and body growth were normal during the test period, and gross necropsies did not reveal any detectable abnormalities in the vital organs or at the applied region (FIG. 10A).

Figure 10B:
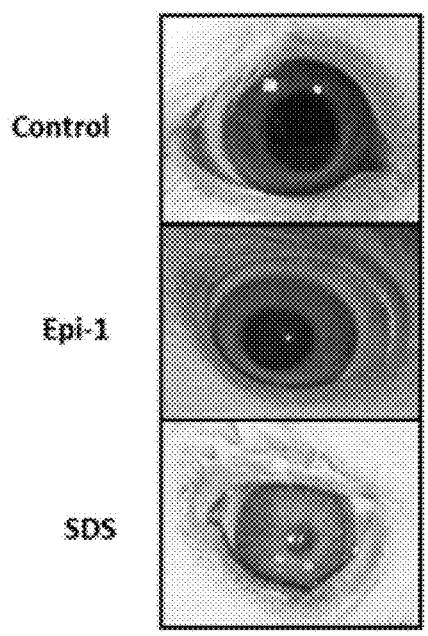

Next, eye irritation tests were performed using rabbits. Eyes were subjected to 1 mg/eye/day of Epi-1 for 7 days, and left to recover for 7 days. On days 2 and 3, Epi-1-instilled eyes exhibited signs of lacrimation, but later the eyes became normal and did not show any significant ocular signs (Table 2) when compared with SDS-treated eyes (positive irritant) during the test period. Necropsies did not reveal any abnormalities. Overall, we conclude that Epi-1 does not cause any adverse toxicity when administered through oral, dermal, or ocular routes (FIG. 10B).

TABLE 2

Results of Eye irritation tests for Epi-1

| Clinical symptoms | Grade | |
|---|---|---|
| | SDS | Epi-1 |
| Corneal opacity | 2 | 0 |
| Iris lesion | 0 | 0 |
| Redness of conjunctivae | 1 | 0.1 |
| Reversibility | No | yes |

It was concluded that Epi-1 does not cause adverse effects when administered through the tested routes in mice and rabbits. It was previously found that Epi-1 was involved in wound healing during skin injury; and no adverse effects were observed in the systemic toxicity study in mice. Thus, Epi-1 is suitable for systemic, oral, or topical applications.

Example 2

Study on TP4

2.1 Materials and Methods 2.1.1 *H. pylori* strains and other materials

*H. pylori* strains American type cell cultures (ATCC) 43504, 51653, and 700392, and a clinical isolate CI-HC-028 provided by Dr. Ming-Shiung Wu, (Department of Internal Medicine, Gastrointestinal Hepatobilary Division, National Taiwan University Hospital, Taiwan) were used to determine the antimicrobial efficacy of TP4. *H. pylori* growth under a microaerobic atmosphere using Anaeropack-Anaero packs (Mitsubishi, Japan). Antibiotics; amoxicillin, clarithromycin and metronidazole (Sigma Chemical Co., St. Louis, Mo.). All animal protocols number 96025 were approved by the Institutional Animal Care and Use Committee (IACUC), College of Science, National Taiwan Ocean University, Keelung, Taiwan.

2.1.2 Synthesis of the Antimicrobial Peptide TP4

Nile tilapia piscidin 4 (TP4) having the amino acid sequence of FIHHIIGGLFSAGKAIHRLIRRRRR (SEQ ID NO: 6), was synthesized by GL Biochem (Shanghai, China) using a solid-phase procedure of Fmoc chemistry. The crude peptides were extracted, lyophilized, and purified by reverse-phase high-performance liquid chromatography (HPLC). The molecular masses and purities of the purified peptides were verified by mass spectroscopy and HPLC, respectively. The synthetic peptides at >95% purity were freshly reconstituted in PBS for working stocks prior to each experiment.

2.1.3 Anti-*H. pylori* Assessment in vitro

*H. pylori* cells undergoing exponential growth were suspended in sterile phosphate-buffered saline (PBS), and adjusted to 0.05 OD using BHI broth; the inoculum was dispensed onto a microtitre plate. Peptide TP4 was prepared at various concentrations (0.04 to 50 µg mL-1) using PBS. Antibiotic resistant clinical isolate CI-HC-028 and three reference strains were used for susceptibility testing. The MIC was defined as the lowest concentration of the drug at which there was no visible growth. For quality control and comparative analyses, the susceptibility of all four *H. pylori* strains to the antibiotics amoxicillin, clarithromycin, and metronidazole were also examined.

2.1.4 Dose and Time-dependent Effects of TP4

TP4 peptide solutions (100 µl) at concentrations corresponding to ¼, ½, 1, 2, and 4 fold the MIC were prepared and added to an equal volume of solution containing *H. pylori* counts of approximately $10^7$ CFU mL-1 onto a microtitre plate. The plates were incubated at 37° C., and samples were collected at 1, 3, 6, 12, and 24 h and plated with appropriate dilutions onto blood agar plates; bacterial counts were enumerated and expressed as mean log (CFU mL-1) with standard error.

2.1.5 Effect of TP4 on *H. pylori* Surface Charge

Zeta potential studies were performed at room temperature using a Zetasizer Nano ZS (Malvern Instruments, Worcestershire, UK) equipped with a 633-nm HeNe laser. TP4 at the MIC was prepared. A 100 µl volume of each peptide stock dilution was added to 900 µl (0.5 OD) of *H. pylori* in liquid culture/blood agar cultures. Positive controls contained filtered buffer instead of peptide. The bacterial suspensions were dispensed into disposable zeta cells with gold electrodes, and allowed to equilibrate for 15 min at 25° C. The zeta potential for each sample was calculated. The complete experiment was carried out twice for each peptide using independently grown cultures.

2.1.6 Transmission Electron Microscopy (TEM) Analysis of TP4-induced Morphological Changes in *H. pylori*

Transmission electron microscopy (TEM) was used to examine the TP4 mechanism of action on *H. pylori*, overall cell morphology, TP4 translocation into *H. pylori*, and interaction of TP4 with internal targets. *H. pylori* overnight cultures from BHI-blood agar plates were collected, and 0.1 OD inocula were incubated with TP4, Amoxicillin, and/or PBS (PBS only: negative control). At 6 h of culture, *H. pylori* cells were collected and successively washed twice in PBS by centrifugation and resuspension. The cells were then fixed and processed for TEM using previously described methods, with some modifications. Briefly, cells were dehydrated in a graduated series of ethanol, followed by resin polymerization at 65° C. for 3 days. An EM ultramicrotome was used to slice thin sections of 70- to 80-nm thickness from the polymerized blocks, which were then loaded on 400-mesh copper grids. The sections were post stained with 2% uranyl acetate for 15 min and then lead citrate for 5 min, before being mounted for observation using an FEI Tecnai G2 F20 S-TWIN transmission electron microscope (FEI Company, Hillsboro, Oreg.) operating at 80 keV. The morphology of the cells was observed at low-power magnification (×1100), and the cell wall ultrastructure was observed at high-power magnification (×2, 500/5,000/7,000, or ×15, 000). Each grid was scrutinized with the same settings. Images were recorded with a 4MP SPOT Insight charge-coupled-device (CCD) camera.

2.1.7 Monotherapeutic Efficacy of TP4 against *H. pylori* Infection in a Mouse Model Male C3H/HeN mice were obtained from BioLASCO Tawian, co., Ltd., and housed at the Laboratory Animal Facility. Mice were maintained in pathogen-free sterile isolators, according to the guidelines of the Council of Agriculture (COA, Taiwan). All animal protocols with reference number 96025 were approved by the Institutional Animal Care and Use Committee (IACUC) of the College of Science, National Taiwan Ocean University. Keelung, Taiwan. For the *H. pylori* infection model, six-week-old male mice were randomly divided into three groups of six mice each. To establish primary *H. pylori* infection, mice were intragastrically challenged with ~1×$10^9$ CFU of *H. pylori* on two days (with 24 h interval. After colonization (day 9 onwards), the mice were treated with a monotherapeutic dose of TP4 (8 mg/kg) every day for 14 days; the control group received an equivalent volume of PBS. Mice were sacrificed 2 wk posttreatment on day 22, and the gastric tissue was processed for urease activity, quantification of *H. pylori*, Western blot, histopathology analysis, T cell subset quantification, and real-time PCR.

2.1.8 Assessment of *H. pylori* Colonization

Harvested stomach lysates were prepared and serially diluted, and 100 µl aliquots were spread onto EYE selective agar plates in duplicate. The plates were incubated under microaerophilic conditions at 37° C. for 24-72 hr. Pink colonies (*H. pylori*) and total viable counts were recorded.

2.1.9 Expression of *H. pylori* Virulence Factor Genes

Genomic DNA (gDNA) was isolated from gastric tissue lysates (25 µl) using the Tissue and Cell Genomic DNA Purification Kit (GeneMark; DP021-50, Taiwan). The concentration and quality of the DNA was determined using a NanoDrop N1000 spectrophotometer. Polymerase chain reaction (PCR) was performed using gene specific primers (UreB F: 5'-GGC ACC ACT CCT TCT GCA AT-3' (SEQ ID NO: 10) R: 5'-CAG CTG TTT GCC AAG TTC TGG-3' (SEQ ID NO: 11), CagA F: 5'-GAT GTG AAA TCC CCG GGC TC-3' (SEQ ID NO: 12), R: 5'-ACT GCG ATC CGG ACT ACG AT-3' (SEQ ID NO: 13), internal control 16s rRNA F: 5'-ACG CGT CGA CAG AGT TTG ATC CTG GCT-3' (SEQ ID NO: 14) R: 5'-AGG CCC GGG AAC GTA TTC AC-3') (SEQ ID NO: 15) and 100 ng of gDNA as template. The resulting PCR products were separated by electrophoresis on a 2% agarose gel and stained with ethidium bromide.

2.1.10 Western Blotting

Urease B protein was used as a marker to confirm the presence of *H. pylori* in gastric tissue. Total lysate protein (25 µg) was loaded onto a SDS gel and separated by electrophoresis. The protein bands were then transferred onto a PVDF membrane. After blotting, the membrane was blocked with 3% BSA in TBS with 0.01% Tween 20, and proteins were detected using Urease B specific antibody. A chemiluminescence detector (UVP BioSpectrum) was used to determine the relative intensity of the protein bands.

2.1.11 Histopathology Examination

Gastric tissue biopsies were fixed in buffered paraffin and embedded in paraffin wax. A section of about 5 μm was stained with hematoxylin and eosin to analyze tissue inflammation. For staining against *H. pylori*, tissue slides were deparaffinized with xylene and alcohol, and then rehydrated in water. After washing in PBS, the tissue section was incubated with modified Giemsa stain for 2-5 minutes, and then washed with PBS. Slides were fixed, and sections were observed at different magnifications under light microscopy. The tissues were evaluated as described previously.

2.1.12 Flow Cytometry

Flow cytometry was performed to quantify mice splenic T cell subsets. Briefly, splenectomies were performed on euthanized mice, and the spleens were transferred into RPMI media. Spleens were minced and passed through a 100μ size mesh at room temperature, and the single cell suspensions were pelleted at 1500 rpm for 5 min. The resulting cell pellet was resuspended in 3 ml of RBC lysis buffer, and incubated for 5 min at room temperature (RT) with gentle tapping to assist in lysis and cell disintegration. The lysis reaction was stopped by diluting the buffer with RPMI media. The mixture was centrifuged again, and the pellet was resuspended in RPMI media. The resulting single cell suspension was aliquoted into flow cytometry tubes (100 μl/tube). One microliter of fluorescent dye-labeled monoclonal antibody (T-cell subsets; CD4, Th17, Treg) was added to each tube, and the volume was made up to 500 μl with PBS. The tubes were covered with foil and incubated in the dark for 1 hr at room temperature. The samples were then analyzed using a BD FACS Canto-A flow cytometer, and the percentages of T cell subsets were recorded.

2.1.13 Gastric Cytokines and T Cell Marker Gene Expression

Total RNA from stomachs of C3H/HeN mice was prepared using the High Pure RNA Tissue Kit according to the recommendations of the manufacturer (Roche, USA). For cytokine mRNA quantification, 5 μg of total RNA was converted into cDNA using a high capacity cDNA archive kit (Invitrogen). Levels of interleukin IL-1β, IL-6, IL-18, IL-10, IL-23, IL-17, tumor necrosis factor alpha (TNF-α), TGF-β, and FoxP3 mRNA were measured by Q-PCR using TaqMan gene expression assays for use in the A CFX Connect™ Real-Time PCR Detection System (Bio-Rad). Transcript levels were normalized to those of mRNA of the endogenous control glyceraldehyde-3-phosphate dehydrogenase (GAPDH), and expressed as the fold change compared to samples from control mice using the Comparative CT method (Bio-Rad).

2.1.14 Toxicity Studies of TP4

Oral Toxicity:

Acute toxicity was assessed in C3H/HeN mice with 6 animals per group, by single oral administration of TP4 (125 mg/kg). After dose administration, the animals were kept under observation for a minimum of 48 hr and the mortality rate and clinical signs were recorded. Subacute toxicity: animals were administered with TP4 (600 μg dose/day) for 14 days. During dose administration, the animals were observed every day for any signs of toxicity for 28 days test period. The morbidity, mortality, and other clinical signs were recorded and assessed.

Dermal Toxicity:

TP4 (125 mg/kg) was applied onto the mouse skin (topical). After administration, the animals were kept under observation for a minimum of 48 h and clinical signs were noted.

Eye Irritation Test in New Zealand White Rabbits:

Healthy young adults rabbit eyes were treated with TP4, PBS (vehicle control), or 0.1% SDS (positive control). A repeated dose of 1 mg/kg every day for 7 days was administered. During the treatment period, the eyes were examined on days 1, 3, 5, and 7, and allowed to recover until day 14. Clinical signs were recorded during the test period, and grades were assigned for ocular reactions during examination.

2.1.15 Statistical Analysis

Statistical analyses were performed and graphs were generated using SPSS 17.0, Graphpad 5.2 software. Results are represented as means±s.e.m. (standard error of the mean). Statistical analyses were performed using Student's t-test, ANOVA. The values of p are significant at $p<0.05$.

2.2 Results 2.2.1 Determination of MIC and MBC for Tilapia Piscidins 1~5 against *H. pylori*

It was demonstrated that the tilapia piscidins were potent against Gram negative and Gram positive pathogens. 25 Here, we investigated the minimal inhibitory concentrations (MICs) of five tilapia piscidins against various *H. pylori* strains, including antibiotic resistant strain. The MIC values are presented in Table 3. With the exception of TP2, the other four peptides (TP1, TP3, TP4, and TP5) inhibited the growth of *H. pylori*. The peptide with strongest efficacy was TP4, and so it was selected for in-depth characterization. The data in Table 3 indicate that all four strains of *H. pylori* are sensitive to TP4 (MIC-1.5-3 μg mL-1), irrespective of whether the strain is sensitive or resistant to antibiotics. Importantly, the effect of TP4 is dose- and time-dependent, indicating that TP4 interacts with a fixed number of bacterial targets.

TABLE 3

Antimicrobial activities of tilapia piscidins 1~5 against laboratory and resistant 552 clinical isolate *H. pylori* strains

| Tilapia Piscidin | | MIC (μg mL-1)[a] *H. pylori* strains | | | |
|---|---|---|---|---|---|
| designation | Sequences[b] | 43504 | 700392 | 43629 | CI-HC-028[b] |
| TP1 | FDWDSVLKGVEGFVRGYF (SEQ ID NO: 7) | >12 | >12 | >12 | >12 |
| TP2 | GECIWDAIFHGAKHFLHRLVNP (SEQ ID NO: 8) | NE[c] | NE | NE | NE |

TABLE 3-continued

Antimicrobial activities of tilapia piscidins 1~5 against laboratory and resistant 552 clinical isolate *H. pylori* strains

| Tilapia Piscidin | | MIC (μg mL-1)[a] *H. pylori* strains | | | |
|---|---|---|---|---|---|
| designation | Sequences[b] | 43504 | 700392 | 43629 | CI-HC-028[b] |
| TP3 | FIHHIIGGLFSVGKHIHSLIHGH (SEQ ID NO: 2) | 8-12 | 8-12 | 8-12 | 8-12 |
| TP4 | FIHHIIGGLFSAGKAIHRLIRRRRR (SEQ ID NO: 6) | 1.5-3* | 1.5-3* | 1.5-3* | 1.5-3* |
| TP5 | QLQGKQVSGEVVQKVLQELIQSVAKP (SEQ ID NO: 9) | >12 | >12 | >12 | >12 |

[a]The minimum inhibitory concentration
[b]CI-HC-028: Clinical isolate
[c]NE: No effect
*All H. pylori strains exhibit significant sensitivity to TP4 (p < .01)

2.2.2 Dose and Time Killing Curves

Figure 11A:
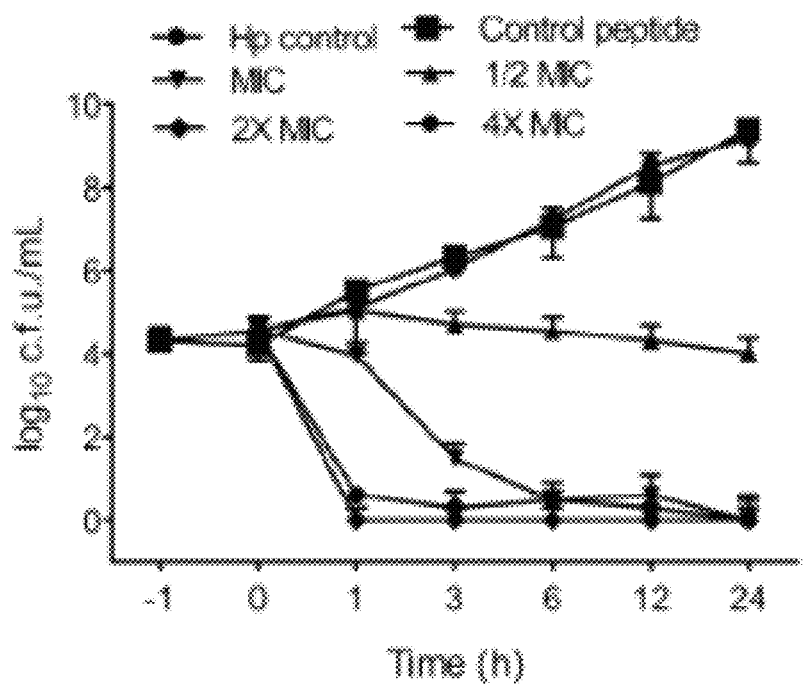
FIG. 11A-11D show the effects of TP4 on the sensitive and resistant *H. pylori* strains.

The rate of antimicrobial activity is important, as it determines whether the required concentration is maintained for sufficient time in a harsh gastric environment. Therefore, we analyzed dose dependent effect against *H. pylori* and were found to be 99% and 99.99% at MIC and 2×MIC, respectively. Further, we evaluated time-kill assay against *H. pylori* strain. As shown in FIG. 11A, no colonies were recovered after treatment with 1×MIC of TP4; the time required to establish a 99% killing rate was about 3 h. Incubation with 2 or 4×MIC increased the killing rate. Taken together, these data indicate that TP4 acts in a dose- and time-dependent manner against *H. pylori*. Rapid killing kinetics by AMPS occur via membrane lysis/pore formation.

2.2.3 TP4 Antimicrobial Activity is Independent of Antibiotic Resistance

Figure 11B:
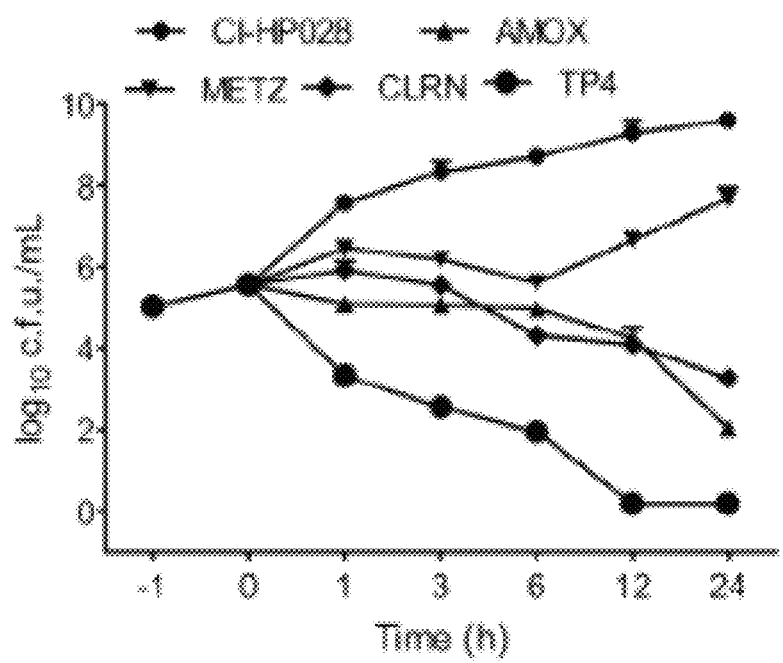

The bactericidal activities of TP4 and conventional antibiotics against resistant clinical isolate CI-HC-028 were compared. Certain resistant strains of *H. pylori* was previously reported to be resistant to metronidazole and clarithromycin 27. Here, we examined time-based susceptibility profiles of CI-HC-028 shown in FIG. 11B; by ~6 hr, TP4 treatment had reduced *H. pylori* >3 log orders (99%), while, of the antibiotics, only amoxicillin showed 90% killing within 24 hr. Metronidazole caused an initial decrease in cell count, but gradually lost activity; clarithromycin consistently reduced cfu, but the time taken to 90% reduction was >24 hr. Thus, there is no correlation between multidrug resistant (MDR) phenotype and vulnerability to TP4. Therefore, TP4 is more effective than antibiotics against MDR *H. pylori*.

2.2.4 Development of Drug Resistance

Figure 11C:
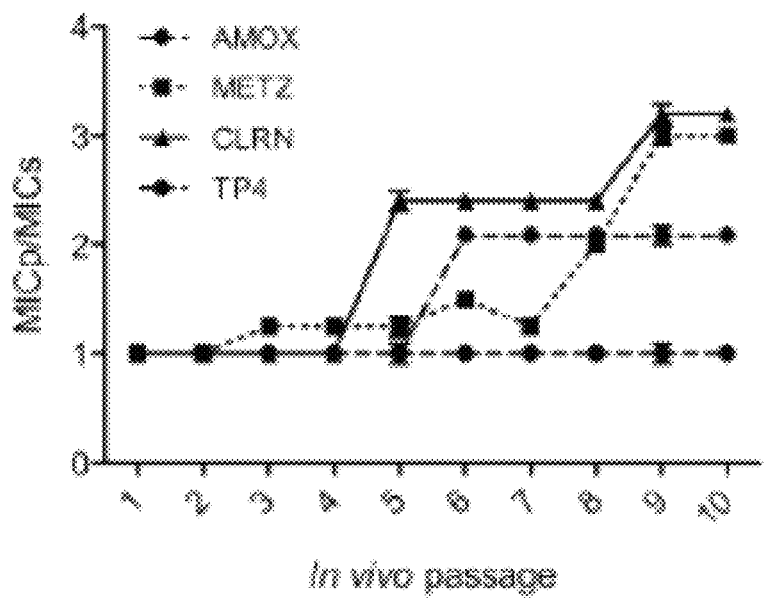

A major driver of drug resistance development is inappropriate antibiotic use and poor compliance with therapeutic regimens. 28 Here, we established a model for simulating conditions of drug resistance emergence: bacteria were exposed to sub-inhibitory doses of antibiotics (AMOX, CLRN, METZ), or peptide TP4 in vitro (see supplementary material methods). As shown in FIG. 11C, the drug resistance index (drug resistance index: MICp/MICs); for amoxicillin increased slightly after passage 6, and remained constant thereafter. For clarithromycin and metronidazole, the resistance indices (MIC) gradually increased from passage 3 to the last passage. However, the resistance index for TP4 did not change during the course of our experiment. These findings suggest that bacteria may not readily develop resistance to TP4 peptide.

2.2.5 TP4 Exhibits Synergistic Activity with Antibiotics against Resistant *H. pylori*

Figure 11D:
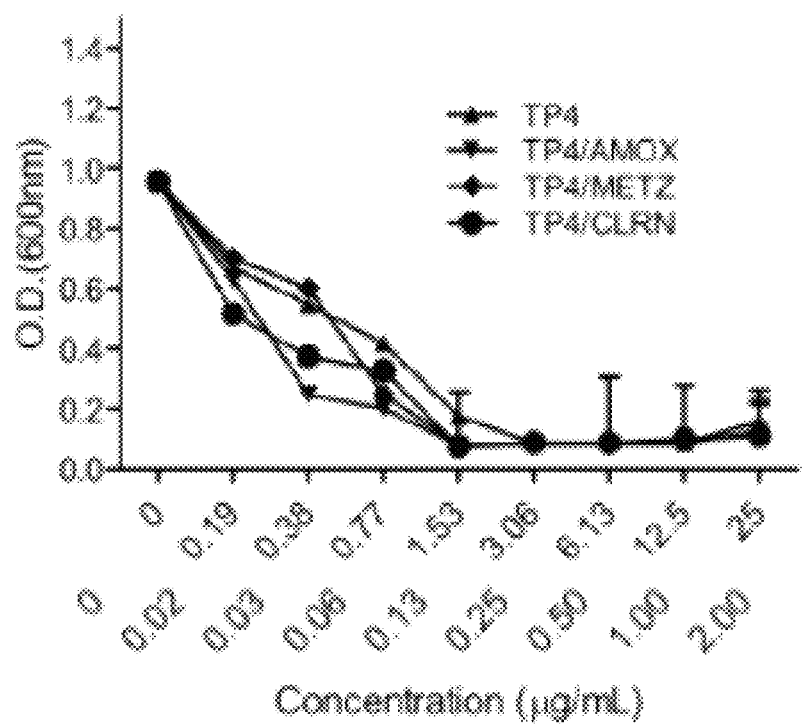

Combination therapy often enhances antibiotic efficacy and mitigates the frequency at which drug resistance emerges. To determine the suitability of TP4 for combination therapy, we examined whether this AMP exhibits synergistic activity with different classes of antibiotics. The in vitro dose-OD fall kinetics was evaluated to determine the activity of TP4 in combination with AMOX, CLRN, or METZ, which are traditionally used as the first line of defense against *H. pylori*. It was reported that TP4 has a significant synergistic effect, reducing the MIC of AMOX by one-fourth, and for METZ and CLRN by one-half folds (FIG. 11D).

2.2.6 In vitro Antimicrobial Mechanism of TP4 Via Membrane Micellization: NPN Fluorescence, Surface Charge and Transmission Electron Microscopy Studies.

Figure 12A:
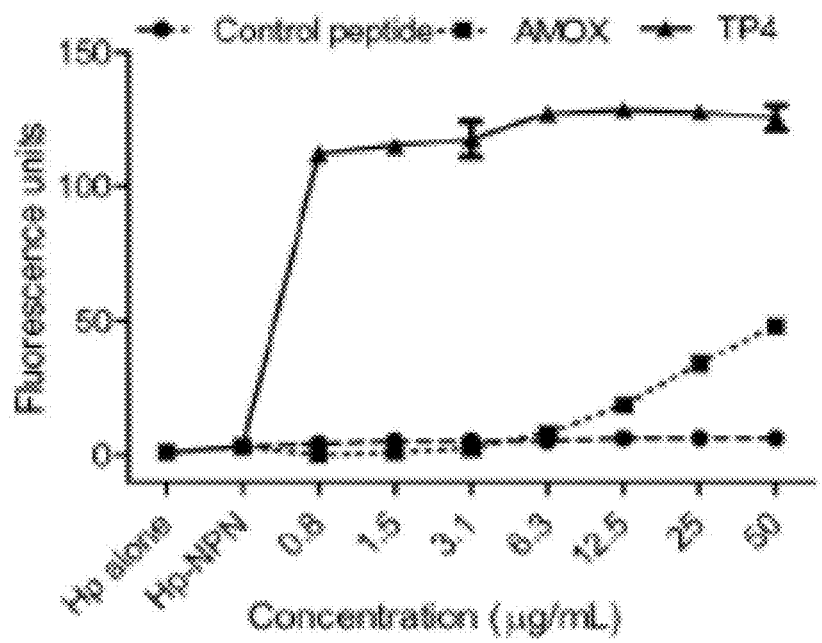
FIG. 12A-12D show the mechanism of action of TP4 on *H. pylori* membrane via micellization and leakage of cellular constituents.

Cationic AMPs have been shown to target and disrupt bacterial membranes and/or interact with internal targets in a manner that may interrupt biomolecule synthesis. Thus, we examined whether TP4 induces permeation and disruption of the *H. pylori* cell membrane. We assessed membrane integrity using 1-N-phenylnaphthylamine (NPN) uptake assay. Generally, NPN is omitted by intact bacterial cell membranes. However, when membrane assembly is disrupted, NPN easily passes through the barrier into the hydrophobic interior of the outer membrane, resulting rapid increase in fluorescence. We thus examined NPN fluorescence intensity following TP4 treatment (FIG. 12A). TP4 increased fluorescence at sub-MIC values; thus, this AMP can effectively permeabilize the membrane at sub-MIC doses. However, AMOX shows a slight increase in fluorescence intensity only at high doses. To confirm that TP4 permeabilize the cell membrane, we analyzed the surface charge (zeta potential/mV) of the bacterial culture through zeta potential studies (FIG. 12B). *H. pylori* blood agar and broth inoculums displayed zeta potentials of −33.83 and −27.47 mV, respectively. Addition of TP4 at the MIC to both inoculums dramatically increased the zeta potential to +13.03 and −6.18 mV, respectively. These data strongly suggest that TP4 interacts with the *H. pylori* surface membrane, and thereby lyses the membrane.

2.2.7 the Effect of TP4 on *H. pylori* Membrane Morphology

Figure 12B:
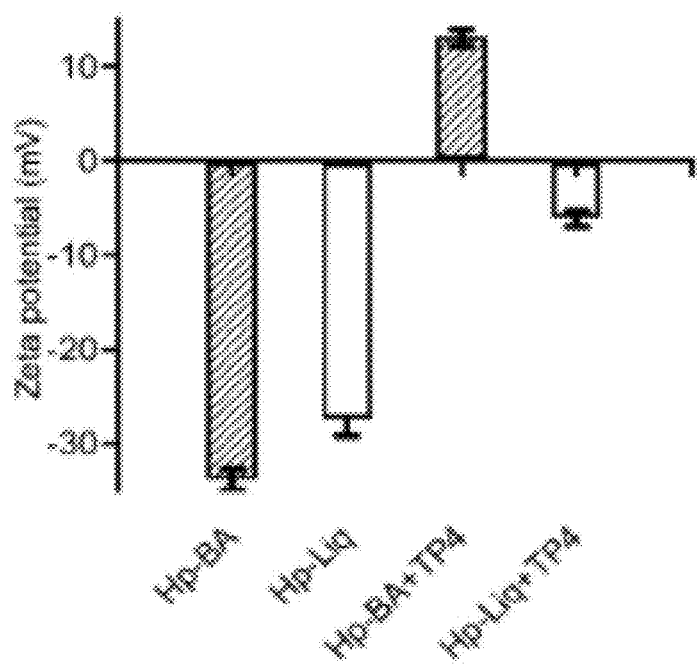
Figure 12C:
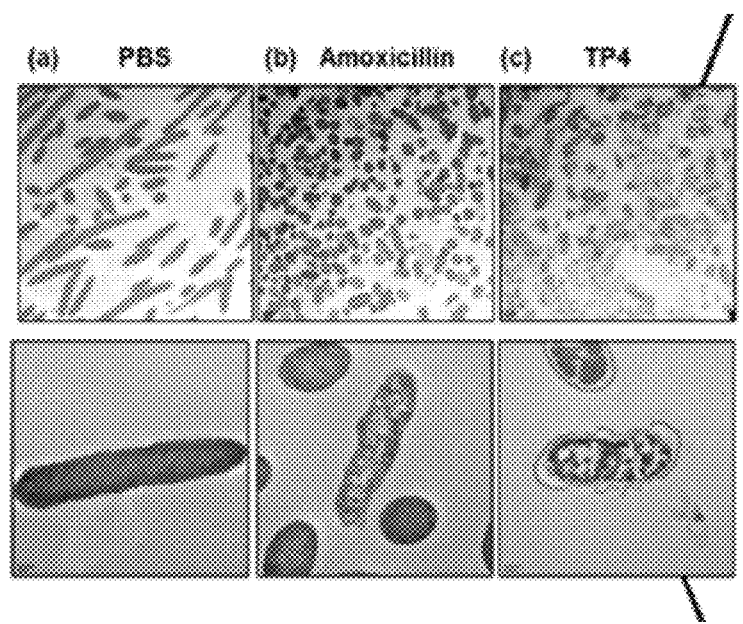
Figure 12D:
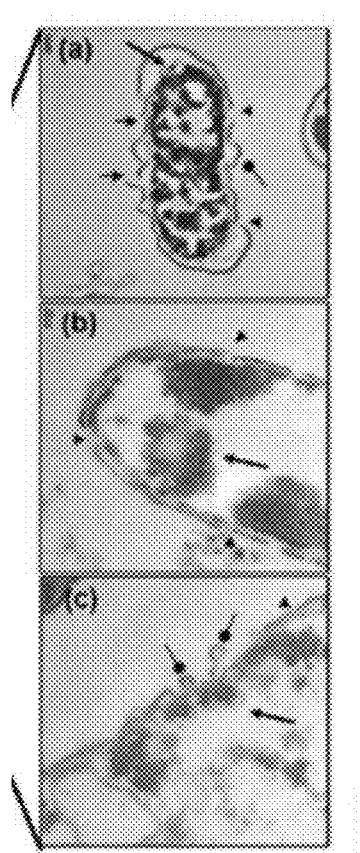

Next, TEM was used to inspect the ultrastructure of cells harvested at 2 h post exposure with TP4. Low and high-magnification images of control *H. pylori* cells reveal long, regular spiral structures, and circular coccoid cells with intact cell membranes, respectively (FIG. 12C, (a)). Upon exposure to AMOX (FIG. 12C, (b)), *H. pylori* appeared as 'ghost' cells, with loose outer membranes. On the other hand, TP4 resulted in substantial disruption of bacterial cell membranes (FIG. 12C, (c)); high-magnification images revealed this to be due to micellization (FIG. 12D). Additionally, electron-dense structures were observed. The effects of TP4 at this early time point are consistent with the observed NPN membrane permeabilization time (FIG. 12A) and the kill kinetics assay data (FIG. 11A).

Figure 16:
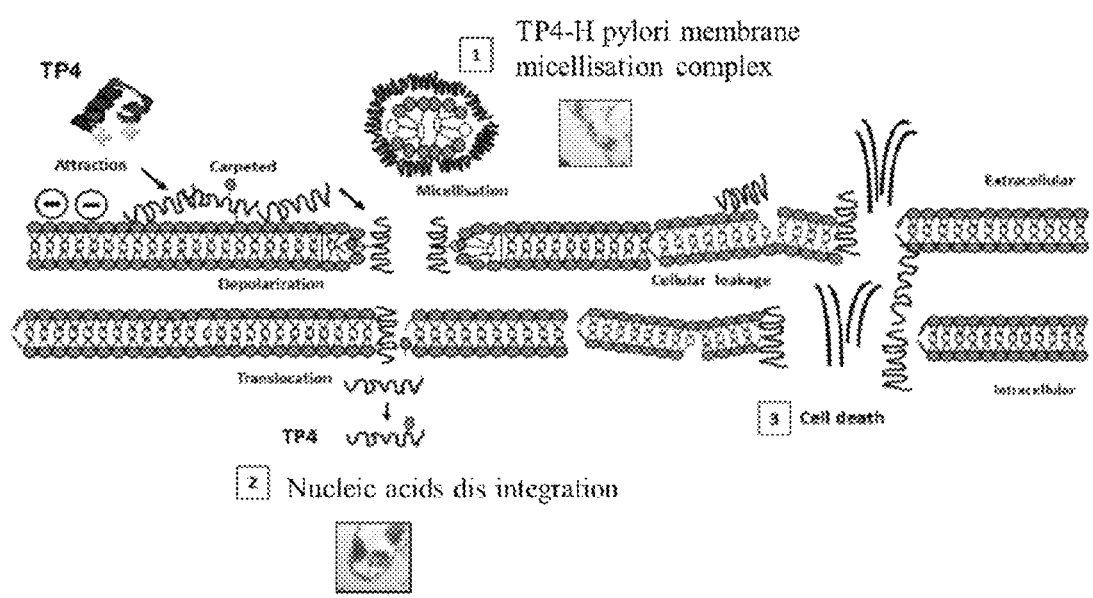
FIG. 16 shows the proposed mechanism of action of TP4 against *H. pylori*. including 1) Membrane micellization, 2) Translocation and DNA disintegration, 3) Cellular leakage of essential respiratory ions causes osmotic imbalance, and subsequent cell death.

2.2.8 Efficacy of the Antimicrobial Peptide TP4 against *Helicobacter pylori* Infection Surprisingly, at higher magnifications (×7000-15000), The extensive membrane perturbation of *H. pylori* was observed (FIG. 12D), consistent with the appearance of protruding micelles, membrane sloughing (FIG. 12D, (a)). In addition, missing membrane sections was observed (FIG. 12D, (b)) and nicks indicative of micellization, as well as detachment of bacterial-TP4 micelles (FIG. 12D, (c)). Outer membrane destruction was evidenced as the formation of micelles, which in turn lead to the leakage and membrane depolarization; as expected, the morphology correlates with zeta potential (FIGS. 12A and 12B). Taken together, it was the first time to show based on these data that TP4 caused *H. pylori* cell death by inducing micellization of cell membranes. The proposed mechanism of action is given in FIG. 16.

Figure 13A:
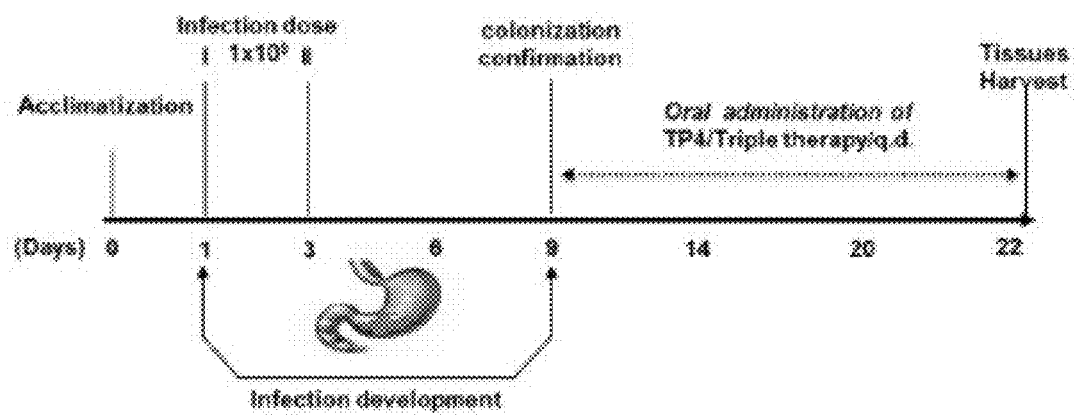
FIG. 13A-13D show the efficacy of TP4 on *H. pylori* infection mouse model.
Figure 13B:
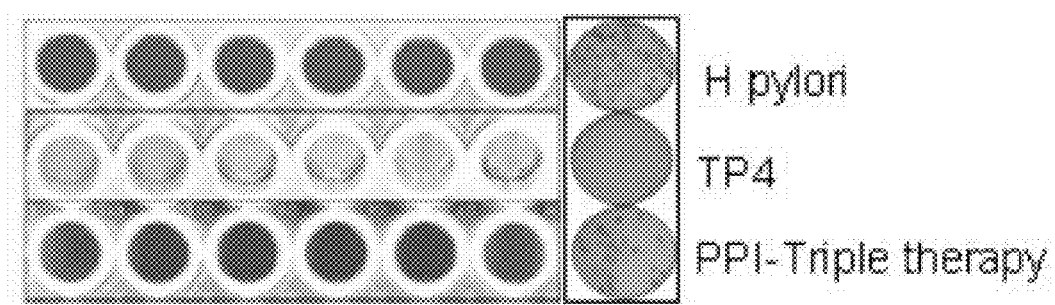
Figure 13C:
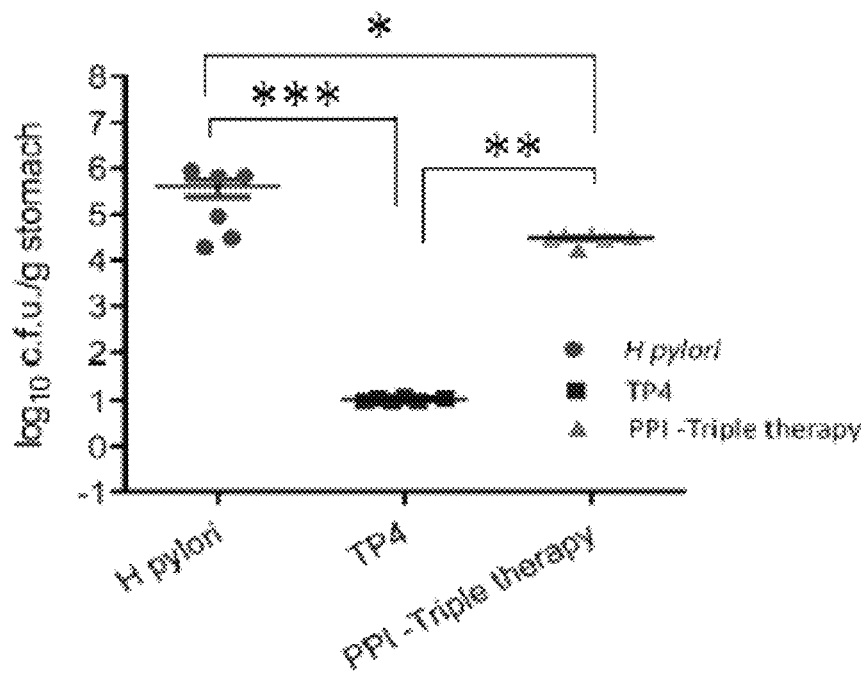

2.2.9 In vivo Efficacy of TP4 against *H. pylori* in a Mouse Model of Infection The in vitro data described above suggest that TP4 has strong activity against *H. pylori*. Thus, we proceeded to evaluate the in vivo therapeutic efficacy and immunomodulatory properties of TP4 against *H. pylori*. FIG. 13A show experimental plan to establish in vivo infection, at 1 wk after infection, mice were divided into 3 groups (n=6) and treated with PBS, TP4, or PPI-Triple therapy. After treatment, urease tests were performed and confirm that *H. pylori* was present in the gastric tissue of untreated mice or mice treated with triple therapy, but not of mice treated with TP4 (FIG. 13B). Furthermore, average of $7 \times 10^5$ CFU/g of *H. pylori* was detected in the untreated group mice stomach; this was significantly reduced to $5 \times 10^4$ CFU/g in mice treated with PPI triple therapy (p=0.0187). Bacteria were not detected in the gastric tissue of mice treated with TP4 (although several methods were unable to detect bacteria this group, the probability of bacterial presence was set as <10 CFU for statistical comparison) (FIG. 13C). In comparison with the PPI-triple therapy group, TP4 caused a significant reduction of bacterial burden (p=0.00152). We conclude that TP4 treatment significantly cleared the *H. pylori* burden from the stomachs of infected mice.

Figure 13D:
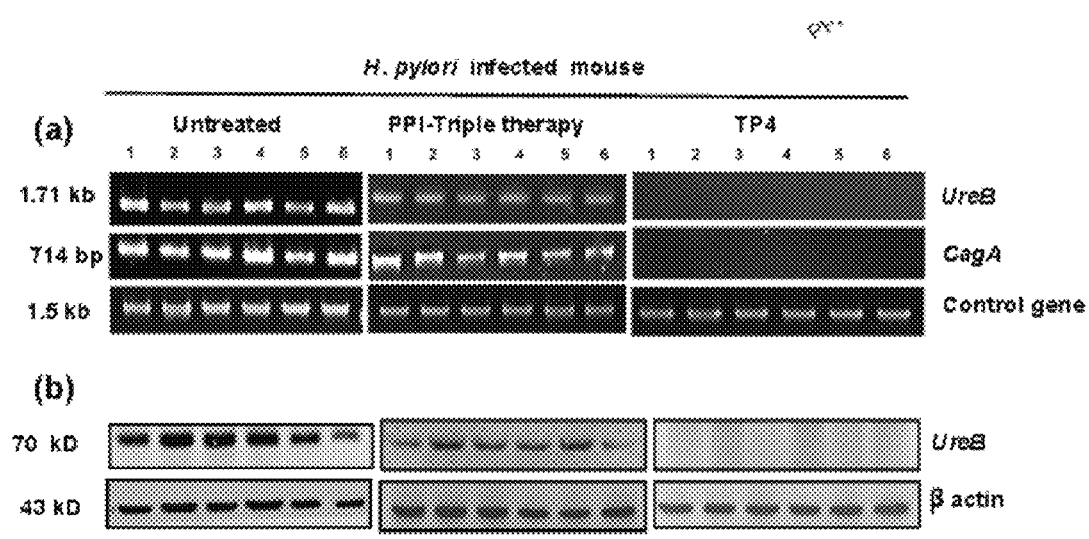

2.2.10 Effects of TP4 on Gene and Protein Expression of *H. pylori* Virulence Factors There is evidence for differing degrees of virulence between *H. pylori* strains, arising from the presence or absence of virulence factors. PCR was used to amplify certain putative virulence markers of *H. pylori* (the cagA and ureB genes) as a sensitive 237 means of detecting *H. pylori* colonization in the stomach (FIG. 13D, (a)). Infected mice sacrificed on day 22 were found to be positive for both ureB and cagA, confirming colonization at the molecular level. Treatment with the antibiotic complex failed to eradicate *H. pylori*, but decreased band intensity (albeit, this decrease was not significant, correlates with FIG. 13C). However, the TP4-treated group tested negative for both the ureB and cagA genes. It was suggested that PCR for ureB and cagA may be suitable for use as a diagnostic tool after therapy, at which time the quantity of bacteria in the gastric mucosa is usually small in number, and may be undetectable by culture or other diagnostic methods. We proceeded to examine gastric lysates for *H. pylori* virulence factor urease B, which is pivotal for colonization in the acidic environment of the stomach. Urease B protein was detected at high intensity in the untreated group, while Triple therapy decreased protein expression, and TP4 treatment abolished detectable protein (FIG. 13D, (b)). These data, together with the membrane and surface charge disruption findings (FIGS. 12A and 12B), suggest that the *H. pylori* virulence factors Cag A and Urease are released through secretory outer membrane vesicles, which are generated from the bacterial membrane and possess the same composition and surface charge as the parent membrane. Thus, TP4 also clears extracellular bacteria and its virulence factors.

2.2.11 Histological Examination and Special Staining Analysis

Figure 14:
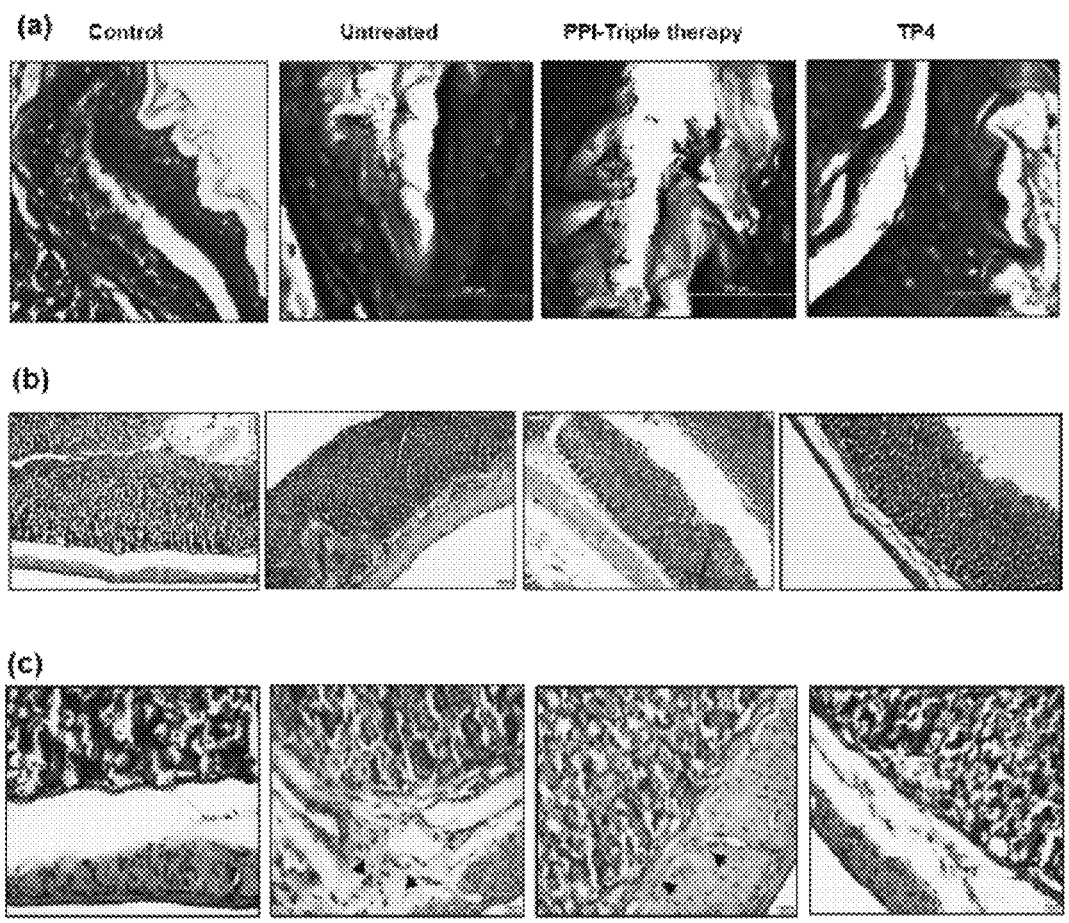
FIG. 14 shows the histopathological evaluation for detection of *H. pylori* and Inflammation in mouse: (a) *H. pylori*-specific staining for the detection of *H. pylori* in gastric sections (red arrows indicated *H. pylori*); (b) Morphological examination during infection and therapeutic mouse by HE staining at low magnification (200×); (c) High magnification (400×):immune cells infiltration at muscularis mucosae (black arrows) (scale bar, 200 µm).

Gastric tissue sections were stained with modified Giemsa for the detection of *H. pylori* colonization of the gastric mucosa (FIG. 14, (a)). Untreated and triple therapy-treated mice exhibited significant *H. pylori* burdens in the gastric surfaces; treatment with TP4 significantly cleared the *H. pylori* burden in gastric tissue. Thus, TP4 treatment significantly reduces the gastric bacterial burden. We then proceeded with HE stained section for histological examination for inflammation (FIG. 14, (b) and (c)). In infected mice, severe inflammation was observed; furthermore, the ulcer crater and muscularis mucosae layer were heavily infiltrated. Inflammatory cells, which infiltrate towards chief and parietal cell regions, cause superficial damage to the surface epithelium due induction of pro- and inflammatory cytokines. Triple therapy did not reduce inflammation. However, treatment with TP4 significantly reduced *H. pylori*-induced inflammation, and significantly reduced immune cell, thereby restoring gastric tissue morphology.

Figure 15A:
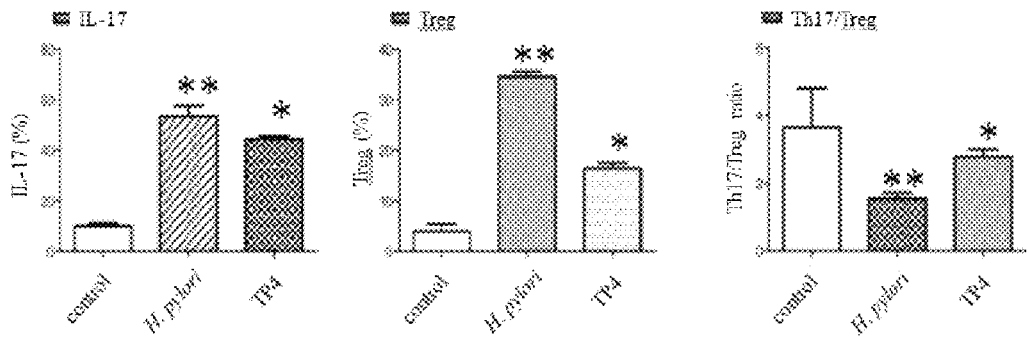
FIGS. 15A and 15B show the immunomodulatory effects of TP4 on *H. pylori*-infected mice, including FIG. 15A showing the splenic T subsets populations were isolated from untreated and treated mice, quantified using fluorescent antibodies against pro-, inflammatory and anti-inflammatory T cells.

2.2.12 Mechanism of Host Immunomodulation Effects of TP4 on Splenic CD4+Foxp3-Treg, Th17 Subsets Dynamics in *H. pylori* Infected Mouse It was previously reported that *H. pylori* infection induces regulatory T cells (Tregs), which leads to *H. pylori* persistence. Foxp3+Tregs and T helper 17 (Th17) cells have been implicated in host immunity to *H. pylori*, particularly at gastric mucosal surfaces. *H. pylori* persistence may depend on the Th17/Treg balance, as mediated by *H. pylori*-interacting antigen presenting cells. *H. pylori* evades immune clearance by modulating the host immune response to maintain low Th17/Treg. In this study, we used flow cytometry to demonstrate that TP4 causes strong inhibition of Treg cells and moderately affects Th17 cells, thereby significantly increasing the Th17/Treg ratio in splenic T subsets (FIG. 15A). By suppressing Treg cells, TP4 treatment dynamically clears *H. pylori* colonization; moreover, a moderate decrease in Th17 cells will also lead to reduced gastric inflammation.

2.2.13 Expression of Gastric Cytokines and T Cell Marker

Figure 15B:
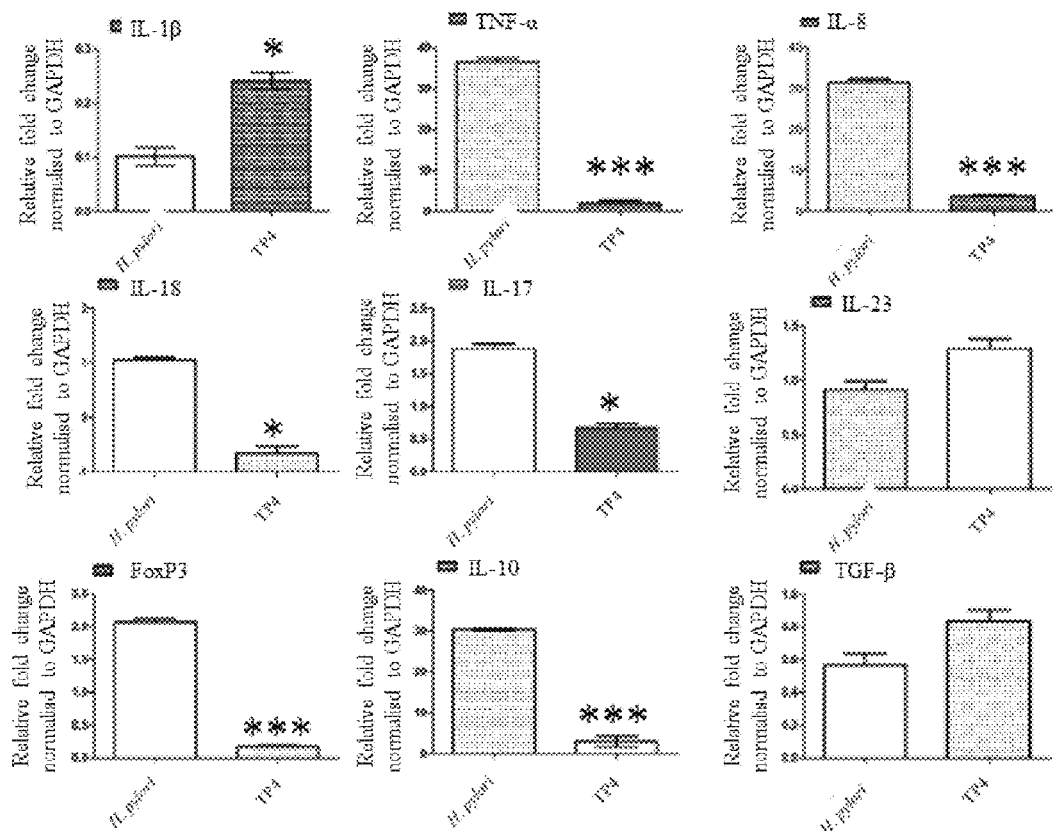

To analyze the immune responses to *H. pylori* infection in our mouse model, we performed gastric tissues mRNA real time RT-PCR to analyze expression levels of cytokines and 285 T cell marker (FIG. 15B). We report that certain cytokines (Tumor necrosis factor-α, IL-6, IL18, IL-10, IL-17, Il-23, and TGF-β) and the T-cell marker FOXp3 were profoundly up-regulated during *H. pylori* infection. Of these cytokines, IL-10, IL-18, and IL-17 play major roles in tenacious *H. pylori* colonization and gastric inflammation. On the other hand, TP4 treatment resulted in down-regulation of all of these genes, with the exceptions of Il-23 and TGF-β. Decreased IL-10 in vivo results in a significant reduction of Treg cells, and restores host Th17/Treg balance.

Further, moderate reduction of IL-17 facilitates the repair of inflamed gastric tissue morphology (Evidence correlated: FIG. 14).

2.2.14 In vivo Toxicity Evaluation of TP4

Acute Oral Toxicity:

A single dose equivalent to 10-fold the in vivo therapeutic dose was orally administered to C3H/HeN mice (n=6), and animal morbidity or mortality was observed for 24 hours. Mice did not exhibit any abnormal clinical signs, and no abnormalities in the vital organs were detected.

Sub-acute Oral Toxicity:

Mice were orally administered with 3-fold therapeutic doses for 14 days. Animals were observed for any clinical signs of morbidity or mortality from days 1 to 28. TP4 did not induce clinical complications in mice, and no abnormalities were observed on day 28 after euthanasia (n=6).

Eye Irritation Test in Rabbits:

A summary of the eye irritation experiment with peptide TP4 is provided in Table 4.

TABLE 4

Eye irritation of TP4 in rabbits
Ocular signs and grading

| Treatment groups | Observation | Corneal opacity | Abnormality iris | Conjunctivae redness | Chemosis |
|---|---|---|---|---|---|
| 50 mg | Day 1 | 0 | 0 | 0 | 0 |
|  | Day 3 | 0 | 0 | 0 | 0.1 |
|  | Day 5 | 0.1 | 0 | 0.1 | 0.1 |
|  | Day 7 | 0.1 | 0 | 0 | 0.1 |
| Recovery | Day 14 | 0 | 0 | 0 | 0 |
| 50S | Day 1 | 1 | 0 | 1 | 1.5 |
|  | Day 3 | 1 | 0 | 1 | 1.5 |
|  | Day 5 | 1 | 0 | 1 | 2 |
|  | Day 7 | 1 | 0 | 1 | 2 |
| Recovery | Day 14 | 0.5 | 0 | 0.5 | 1.5 |

* Data are graded following the grading system of OECD 405 guidelines.

Figure 17A:
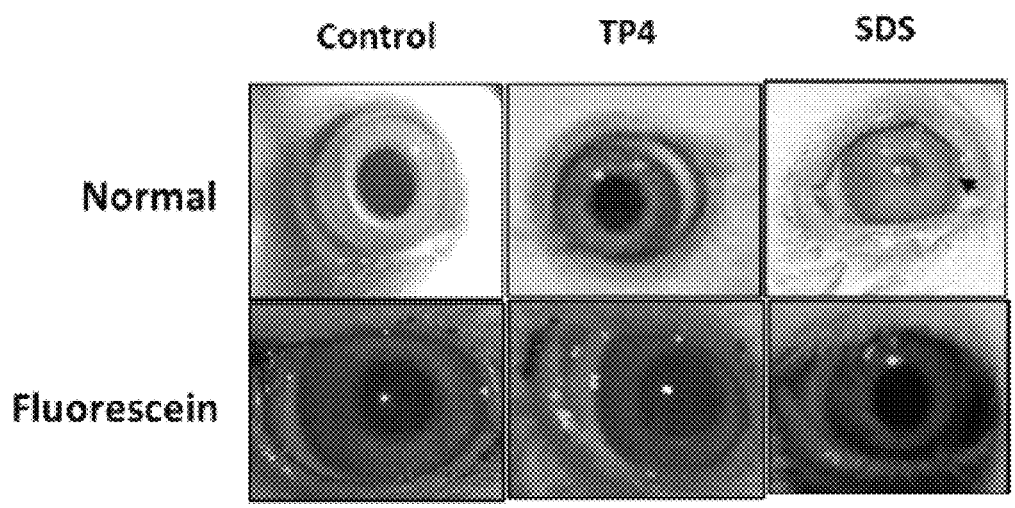
FIGS. 17A and 17B show the TP4 toxicity safety evaluations in New Zealand rabbits and C3H/HeN mice.

No significant clinical signs were observed during the test period (days 1 to 7) when compared to the positive control; the rabbits were sacrificed on day 14, and no abnormalities in the vital organs, nor lesions or clumps in the eyes, were observed (FIG. 17A).

Figure 17B:
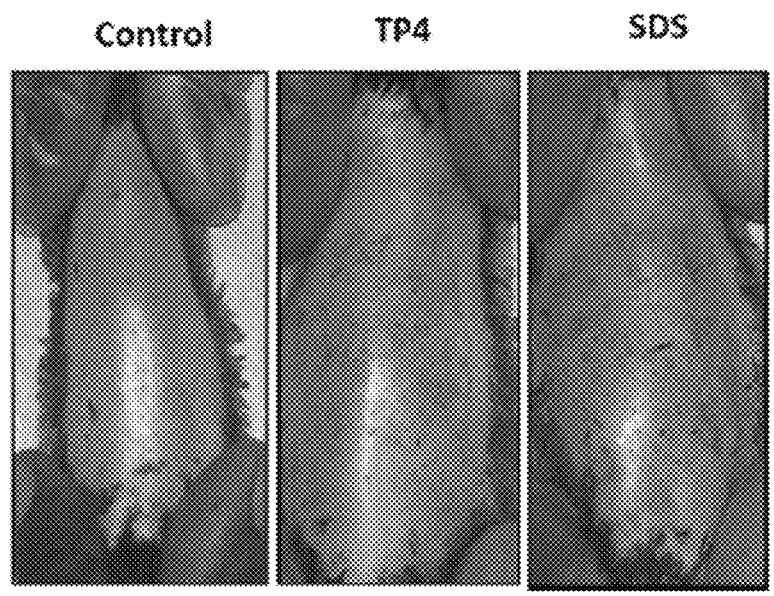

Dermal Toxicity:

No mortality or damaging effects were observed, either immediately or during the 14 days observation period, after dermal exposure of C3H/HeN to TP4 (FIG. 17B). Furthermore, body weight of treated animals was normal until the last day of observation. TP4 treatment did not induce lesions or irritation during the test period, and no gross behavioral changes were observed. Hair growth was also found to be normal, and necropsies did not reveal any gross abnormalities in organ structure or architecture.

In summary, it was demonstrated that TP4 exerts potent antimicrobial activity against *H. pylori* strains (an MDR clinical isolate and standard strain). It is also for the first time evidenced the TP4 mechanism of action via membrane micellization. *H. pylori* infection in mice treated with TP4 was significantly reduced as compared to untreated and conventional antibiotics treated mice. Importantly, high doses of TP4 did not cause any toxicity in mice or rabbits. In addition, TP4 selectively modulated the *H. pylori*-induced immune response by altering the expression of immune-responsive genes. Collectively, these results support the potential development of TP4 as a novel class of anti-*H. pylori* therapeutics.

The descriptions and claims as provided should be understood as of demonstrative purpose instead of limitative in any way to the scope of the present invention.

We claim:

1. A method for treating an infection of *Helicobacter pylori* (*H. pylori*), comprising administering to a subject in need thereof a therapeutically effective amount of an antimicrobial peptide, wherein said antimicrobial peptide is selected from the group consisting of epinecidin-1 (Epi-1), tilapia piscidin 3 (TP3), tilapia piscidin 4 (TP4) and combination thereof.

2. The method of claim 1, wherein the antimicrobial peptide is tilapia piscidin 4 (TP4).

3. A method for treating an infection of multidrug resistant *H. pylori*, comprising administering to a subject in need thereof a therapeutically effective amount of an antimicrobial peptide, wherein said antimicrobial peptide is selected from the group consisting of epinecidin-1 (Epi-1), tilapia piscidin 3 (TP3), tilapia piscidin 4 (TP4) and combination thereof.

4. The method of claim 3, wherein the antimicrobial peptide is tilapia piscidin 4 (TP4).

* * * * *

SEQUENCE LISTING

```
<160> NUMBER OF SEQ ID NOS: 15

<210> SEQ ID NO 1
<211> LENGTH: 20
<212> TYPE: PRT
<213> ORGANISM: Oreochromis mossambicus

<400> SEQUENCE: 1

Gln Ser His Leu Ser Leu Cys Arg Trp Cys Cys Asn Cys Cys Arg Ser
1               5                   10                  15

Asn Lys Gly Cys
            20

<210> SEQ ID NO 2
<211> LENGTH: 23
<212> TYPE: PRT
<213> ORGANISM: Oreochromis niloticus

<400> SEQUENCE: 2

Phe Ile His His Ile Ile Gly Gly Leu Phe Ser Val Gly Lys His Ile
1               5                   10                  15

His Ser Leu Ile His Gly His
            20

<210> SEQ ID NO 3
<211> LENGTH: 21
```

-continued

```
<212> TYPE: PRT
<213> ORGANISM: Epinephelus coioides

<400> SEQUENCE: 3

Gly Phe Ile Phe His Ile Ile Lys Gly Leu Phe His Ala Gly Lys Met
1               5                   10                  15

Ile His Gly Leu Val
            20

<210> SEQ ID NO 4
<211> LENGTH: 33
<212> TYPE: PRT
<213> ORGANISM: Pardachirus marmoratus

<400> SEQUENCE: 4

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu

<210> SEQ ID NO 5
<211> LENGTH: 25
<212> TYPE: PRT
<213> ORGANISM: Chrysophrys major

<400> SEQUENCE: 5

Phe Phe Gly Trp Leu Ile Lys Gly Ala Ile His Ala Gly Lys Ala Ile
1               5                   10                  15

His Gly Leu Ile His Arg Arg Arg His
            20                  25

<210> SEQ ID NO 6
<211> LENGTH: 25
<212> TYPE: PRT
<213> ORGANISM: Oreochromis niloticus

<400> SEQUENCE: 6

Phe Ile His His Ile Ile Gly Gly Leu Phe Ser Ala Gly Lys Ala Ile
1               5                   10                  15

His Arg Leu Ile Arg Arg Arg Arg Arg
            20                  25

<210> SEQ ID NO 7
<211> LENGTH: 18
<212> TYPE: PRT
<213> ORGANISM: Oreochromis niloticus

<400> SEQUENCE: 7

Phe Asp Trp Asp Ser Val Leu Lys Gly Val Glu Gly Phe Val Arg Gly
1               5                   10                  15

Thr Phe

<210> SEQ ID NO 8
<211> LENGTH: 22
<212> TYPE: PRT
<213> ORGANISM: Oreochromis niloticus

<400> SEQUENCE: 8

Gly Glu Cys Ile Trp Asp Ala Ile Phe His Gly Ala Lys His Phe Leu
1               5                   10                  15
```

His Arg Leu Val Asn Pro
            20

<210> SEQ ID NO 9
<211> LENGTH: 26
<212> TYPE: PRT
<213> ORGANISM: Oreochromis niloticus

<400> SEQUENCE: 9

Gln Leu Gln Gly Lys Gln Val Ser Gly Glu Val Val Gln Lys Val Leu
1               5                   10                  15

Gln Glu Leu Ile Gln Ser Val Ala Lys Pro
            20                  25

<210> SEQ ID NO 10
<211> LENGTH: 20
<212> TYPE: DNA
<213> ORGANISM: Artificial Sequence
<220> FEATURE:
<223> OTHER INFORMATION: UreB F primer

<400> SEQUENCE: 10
ggcaccactc cttctgcaat                                              20

<210> SEQ ID NO 11
<211> LENGTH: 21
<212> TYPE: DNA
<213> ORGANISM: Artificial Sequence
<220> FEATURE:
<223> OTHER INFORMATION: UreB R primer

<400> SEQUENCE: 11
cagctgtttg ccaagttctg g                                            21

<210> SEQ ID NO 12
<211> LENGTH: 20
<212> TYPE: DNA
<213> ORGANISM: Artificial Sequence
<220> FEATURE:
<223> OTHER INFORMATION: CagA F primer

<400> SEQUENCE: 12
gatgtgaaat ccccgggctc                                              20

<210> SEQ ID NO 13
<211> LENGTH: 20
<212> TYPE: DNA
<213> ORGANISM: Artificial Sequence
<220> FEATURE:
<223> OTHER INFORMATION: CagA R primer

<400> SEQUENCE: 13
actgcgatcc ggactacgat                                              20

<210> SEQ ID NO 14
<211> LENGTH: 27
<212> TYPE: DNA
<213> ORGANISM: Artificial Sequence
<220> FEATURE:
<223> OTHER INFORMATION: 16s rRNA F primer

<400> SEQUENCE: 14
acgcgtcgac agagtttgat cctggct                                      27

<210> SEQ ID NO 15

```
<211> LENGTH: 20
<212> TYPE: DNA
<213> ORGANISM: Artificial Sequence
<220> FEATURE:
<223> OTHER INFORMATION: 16s rRNA primer

<400> SEQUENCE: 15
aggcccggga acgtattcac                                                    20
```